(12) United States Patent
Little et al.

(10) Patent No.: US 6,585,968 B2
(45) Date of Patent: Jul. 1, 2003

(54) ADENOVIRUS VECTORS SPECIFIC FOR CELLS EXPRESSING ALPHA-FETOPROTEIN AND METHODS OF USE THEREOF

(75) Inventors: Andrew S. Little, Los Altos, CA (US); Daniel R. Henderson, Palo Alto, CA (US); Eric R. Schuur, Palo Alto, CA (US); Henry Lamparski, San Mateo, CA (US)

(73) Assignee: Cell Genesys, Inc., Foster City, CA (US)

( * ) Notice: Subject to any disclaimer, the term of this patent is extended or adjusted under 35 U.S.C. 154(b) by 0 days.

(21) Appl. No.: 09/898,883

(22) Filed: Jul. 2, 2001

(65) Prior Publication Data

US 2002/0164799 A1 Nov. 7, 2002

Related U.S. Application Data

(63) Continuation of application No. 09/593,308, filed on Jun. 13, 2000, now abandoned, which is a continuation-in-part of application No. 09/033,428, filed on Mar. 2, 1998, now Pat. No. 6,254,862.
(60) Provisional application No. 60/039,597, filed on Mar. 3, 1997.

(51) Int. Cl.[7] .................. A61K 48/00; C12N 15/861; C12N 5/10; C12N 15/63; C12N 15/64
(52) U.S. Cl. .................. 424/93.2; 424/93.1; 424/93.6; 536/23.1; 536/24.1; 435/320.1; 435/325; 435/366; 435/455; 435/456; 435/457; 435/69.1
(58) Field of Search .................. 435/320.1, 325, 435/366, 455, 456, 457, 69.1; 536/23.1, 24.1; 424/93.1, 93.2, 93.6

(56) References Cited

U.S. PATENT DOCUMENTS

| | | |
|---|---|---|
| 5,302,698 A | 4/1994 | Morinaga et al. |
| 5,328,470 A | 7/1994 | Nabel et al. |
| 5,354,674 A | 10/1994 | Hodgson |
| 5,501,662 A | 3/1996 | Hofmann |
| 5,635,383 A | 6/1997 | Wu et al. |
| 5,648,478 A | 7/1997 | Henderson |
| 5,698,443 A | 12/1997 | Henderson et al. |
| 5,804,407 A | 9/1998 | Tamaoki et al. |
| 5,807,738 A | 9/1998 | Tamaoki et al. |
| 5,827,686 A | 10/1998 | Tamaoki et al. |
| 5,998,205 A | 12/1999 | Hallenbeck et al. |
| 6,254,862 B1 * | 7/2001 | Little et al. .................. 424/93.2 |

FOREIGN PATENT DOCUMENTS

| | | |
|---|---|---|
| CA | 2134994 | 5/1995 |
| EP | 0 415 731 A2 | 3/1991 |
| WO | WO 93/19768 | 10/1993 |
| WO | WO 94/26915 A1 | 11/1994 |
| WO | WO 95/00655 A1 | 1/1995 |
| WO | WO 95/11984 | 5/1995 |
| WO | WO 96/17053 | 6/1996 |
| WO | WO 96/21036 A3 | 7/1996 |
| WO | WO 96/21036 A2 | 7/1996 |
| WO | WO 96/34969 | 11/1996 |
| WO | WO 97/01358 A1 | 1/1997 |
| WO | WO 98/35028 | 8/1998 |

OTHER PUBLICATIONS

Arbuthnot et al., "In vitro and in vivo hepatoma cell–specific expression of a gene transferred with an adenoviral vector" *Human Gene Ther.* 7:1503–1514 (1996).

Arnberg et al., "Fiber genes of adenoviruses with tropism for the eye and the genital tract" *Virol.* 227:239–244 (1997).

Bailey et al., "Cell type specific regulation of expression from the Ad40 E1B promoter in recombinant Ad5/Ad40 viruses" *Virology* 202:695–706 (1994).

Bailey et al., "Enteric adenovirus type 40: Expression of E1B proteins in vitro and in vivo" *Virology* 193:631–641 (1993).

Behringer et al., "Dwarf mice produced by genetic ablation of growth hormone–expressing cells" *Genes Dev.* 2:453–461 (1988).

Berkner and Sharp, "Generation of adenovirus by transfection of plasmids" *Nucl. Acids Res.* 11(17):6003–6020 (1983).

Bett et al., "An efficient and flexible system for construction of adenovirus vectors with insertions or deletions in early regions 1 and 3" *Proc. Natl. Acad. Sci USA* 91:8802–8806 (1994).

Bett et al., "Packaging capacity and stability of human adenovirus type 5 vectors" *J. Virology* 67(10):5911–5921 (1993).

Bischoff et al., "An adenovirus mutant that replicates selectively in p53–deficient human tumor cells," *Science* 274(5286):373–376 (1996).

Braun et al. "Immunogenic duplex nucleic acids are nuclease resistant" *J. Immunol.* 141(6):2084–1089 (1988).

Bridge et al., "Redundant control of adenovirus late gene expression by early region 4" *J. Virol.* 63(2):631–638 (1989).

Chang et al., "Cancer Gene Therapy Using novel tumor specific replication competent adenoviral vectors" Cold Spring Harbor Gene Therapy Meeting, p. 53 (1996).

(List continued on next page.)

*Primary Examiner*—David Guzo
(74) *Attorney, Agent, or Firm*—Linda Judge; Pamela J. Sherwood; Bozicevic, Field & Francis LLP

(57) ABSTRACT

Adenovirus vectors replication specific for cells expressing α-fetoprotein (AFP) and their methods of use are provided. By providing for a transcriptional initiating regulation dependent upon AFP expression, virus replication is restricted to target cells expressing AFP, particularly hepatocellular carcinoma cells. The adenovirus vectors can be used to detect and monitor samples for the presence of AFP-producing cells as well as to kill selectively malignant cells producing AFP.

22 Claims, 17 Drawing Sheets

OTHER PUBLICATIONS

Chaturvedi et al., "Stabilization of triple-stranded oligonucleotide complexes: use of probes containing alternating phosphodiester and stereo-uniform cationic phosphoramidate linkages" *Nucleic Acids Res.* 24(12):2318–2323 (1996).
*Current Protocols in Molecular Biology* (Ausubel et al., eds., 1987) Supp. 30, Section 7.7.18–19, Table 7.7.1.
Emerson et al., "The zonal expression of alpha–fetoprotein transgenes in the livers of adult mice" *Devel. Dynamics* 195:55–65 (1992).
Felgner and Ringold, "Cationic liposome–mediated tranfection" *Nature* 337:387–388 (1989).
Flint "Expression of adenoviral genetic information in productively infected cells" *Biochem. Biophys. Acta* 651:175–208 (1982).
Flint "Regulation of adenovirus mRNA formation" *Advances Virus Research* 31:169–228 (1986).
Frankel et al., "Selection and characterization of ricin toxin A–chain mutations in *Saccharomyces cerevisiae*" *Mol. Cell. Biol.* 9(2):415–420 (1989).
Ghebranious et al., "Developmental control of transcription of the cat reporter gene by a truncated mouse alphafetoprotein gene regulatory region in transgenic mice" *Mo. Reprod. Devel.* 42:1–6 (1995).
Graham et al., "A new technique for the assay of infectivity of human adenovirus 5 DNA" *Virology* 52:456–467 (1973).
Graham et al. "Characteristics of a human cell line transformed by DNA from human adenovirus type 5" *J. Gen. Virol.* 36:59–72 (1977).
Graham, "Covalently closed circles of human adenovirus DNA are infectious" *EMBO Journal* 3(12):2917–2922 (1984).
Graham, "Growth of 293 cells in suspension culture" *J. Genetic Virology* 68:937–940 (1987).
Grand, "The structure and functions of the adenovirus early region 1 proteins" *Biochem. J.* 241:25–38 (1987).
Groupp et al. "Characterization of the distal alpha–fetoprotein enhancer, a strong, long distance, liver specific activator" *J. Biol. Chem.* 269(35):22178–22187 (1994).
Hallenbeck, O. et al., "Novel Tumor Specific Replication Competent Adenoviral Vectors for Gene Therapy of Cancer" *Cancer Gene Therapy,* 3(6):S19–S20 (1996).
Hayashi et al., "Expression of a thyroid hormone–responsive recombinant gene introduced into adult mice livers by replication–defective adenovirus can be regulated by endogenous thyroid hormone receptor" *J. Biol. Chem.* 269(39):23872–23875 (1994).
Huber et al., "VDEPT: An enzyme/prodrug gene therapy approach for the treatment of metastic colorectal cancer" *Adv. Drug Delivery Rev.* 17:279–292 (1995).
Ido et al., "Gene therapy for hepatoma cells using a retrovirus vector carrying herpes simplex virus thymidine kinase gene under the control of human alpha–fetoprotein gene promoter" *Cancer Res.* 55(14):3105–1309 (1995).
Jaffe et al., "Adenovirus–mediated in vivo gene transfer and expression in normal rat liver" *Nat. Genet.* 1:372–378 (1992).
Kanai et al., "Adenovirally directed enzyme prodrug therapy again hepatocellular carcinoma" *Hepatology* 22(4 Part 2):188A Abstract No. 328 (1995).
Kanai et al., "Gene therapy for hepatocellular carcinom: Chemosensitivity conferred by adenovirus–mediated transfer of the suicide gene" *Gastroenterol.* 110(4):A1227 Suppl. (1996).

Kanai et al., "Gene Therapy for an alpha–fetoprotein–producing human hepatoma cells by adenovirus–mediated transfer of the herpes simplex virus thymidine kinase gene" *Hepatology* 23(6):1359–1368 (1996).
Kanai et al., "Prolonged survival of mice bearing disseminated gastric cancer by adenovirus–mediated gene therapy" *Cancer Gene Ther.* 3(6):S32 Abstract No. P–82 (1996).
Kaneko et al., "Adenovirus–mediated gene therapy of hepatocellular carcinoma using cancer–specific gene expression" *Cancer Res.* 5:5283–5287 (1995).
Kaneko et al., "Gene therapy of hepatocellular carcinoma using the alpha–fetoprotein in an adenoviral vector" *Hepatology* 22(4 Part 2):158A Abstract No. 206 (1995).
Katsuragi et al., "A case of gall bladder cancer with high level alpha–fetoprotein" *Japan J. Clin. Radiol.* 34:371–374 (1989).
Kawamoto et al., "Alpha–fetoprotein–producing pancreatic cancer—A case report and review of 28 cases" *Hepato–Gastroentrol.* 39:282–286 (1992).
Koyama et al., "Biochemical characterization of alpha–fetoprotein and other serum proteins produced by a uterine–endometrial adenocarcinoma" *Jpn. J. Cancer Res.* 87:612–617 (1996).
Lamb et al., "Nucleotide sequence of cloned cDNA coding for preproricin" *Eur. J. Biochem.* 148:265–270 (1985).
Latimer et al., "Specificity of monoclonal antibodies produced against phosphorothioate and ribo modified DNAs" *Mol. Immunol.* 32(14/15):1057–1064 (1995).
Le Gal Le Salle et al., "An adenovirus vector for gene transfer into neurons and glia in the brain" *Science* 259:988–990 (1993).
Mastrangeli et al., "Diversity of airway epithelial cell targets for in vivo recombinatn adenovirus–mediated gene transfer" *J. Clin. Invest.* 91:225–234 (1993).
Maxwell et al., "Cloning, sequence determination, and expression in transfected cells of the coding sequence for the tox 176 attenuated diphtheria toxin A chain" *Mol. Cell. Biol.* 7:1576–1579 (1987).
McKinnon, "Tn5 mutatgenesis of the transforming genes of human adenovirus type 5" *Gene* 19:33–42 (1982).
Messing et al., "$P_0$ promoter directs expression of reporter and toxin genes to Schwann cells of transgenic mice" *Neuron* 8:507–520 (1992).
Nakabayashi et al., "A position–dependent silencer plays a major role in repressing alpha–fetoprotein expression in human hepatoma" *Mol. Cell. Biol.* 11(12):5885–5893 (1991).
Nevins, "Mechanisms of viral–mediated trans–activation of transcription" *Adv. Virus Res.* 37:35–83 (1989).
Palmiter et al., "Cell lineage ablation in transgenic mice by cell–specific expression of a toxin gene" *Cell* 50:435–443 (1987).
Peyrottes et al., "Oligodeoxynucleoside phosphoramidates (P–NH$_2$): synthesis and thermal stability of duplexes with DNA and RNA targets" *Nucleic Acids Res.* 24(10):1841–1848 (1996).
Piatak et al., "Expression of soluble and fully functional ricin A chain in *escherichia coli* is temperature–sensitive" *J. Biol. Chem.* 263(10):4837–4843 (1988).
Quantin et al., "Adenovirus as an expression vector in muscle cells in vivo" *Proc. Natl. Acad. Sci. USA* 89:2581–3584 (1992).

Ragot et al., "Efficient adenovirus–mediated transfer of a human minidystrophin gene to skeletal muscle of mdx mice" *Nature* 361:647–650 (1993).

Rodriguez et al., "Prostate attenuated replication competent adenovirus (ARCA) CN706: A selective cytotoxic for prostate–specific antigen–positive cancer cells." *Cancer Res.* 57:2559=2563 (1997).

Rosenfeld et al., "Adenovirus–mediated transfer of a recombinant alpha1–antitrypsin gene to the lung epithelium in vivo" *Science* 252:431–434 (1991).

Rosenfeld et al., "In vivo transfer of the human cystic fibrosis transmembrane conductance regulator gene to the airway epithelium" *Cell* 68:143–155 (1992).

Sakai et al., "The human alpha–fetoprotein gene" *J. Biol. Chem.* 260(8):5055–5060 (1985).

Scaria et al., *Virology* vol. 191, pp. 743–753 (1992).

Schultz et al., "Oligo–2'–fluoro–2'–deoxynucleotide N3'–P5' phosphoramidates: synthesis and properties" *Nucleic Acids Res.* 24(15):2966–73 (1996).

Stratford–Perricaudet et al., "Evaluation of the transfer and expression in mice of an enzyme–encoding gene using a human adenovirus vector" *Human Gene Therapy* 1:241–256 (1990).

Stratford–Perricaudet et al., "Widespread long term gene transfer to mouse skeletal muscles and heart" *J. Clin. Invest.* 90:626–630 (1992).

Swaminathan et al., "Regulation of adenovirus E2 transcription unit" *Curr. Topics in Microbiol. And Immunol.* 199 part 3:177–194 (1995).

Takiff et al., "Propagation and in vitro studies of previously non–cultivable enteral adenoviruses in 293 cells" *Lancet* 11:832–834 (1981).

Tollefson et al., "The 11,600–$M_w$ protein encoded by region E3 of adenovirus is expressed early but is greatly amplified at late stages of infection" *J. Virol.* 66(6):3633–3642 (1992).

Tollefson et al., "The adenovirus death protein (E3–11.6K) is required at very late stages of infection for efficient cell lysis and release of adenovirus from infected cells" *J. Virol.* 70(4):2296–2306 (1996).

Virtanen et al., "mRNAs from human adenovirus 2 early region 4" *J. Virol.* 51(3):822–831 (1984).

Wang et al., "Expression of the APRT gene in an adenovirus vector system as a model for studying gene therapy" *Adv. Exp. Med. Biol.* 309B:61–66 (1991).

Watanabe et al., "Cell Specific enhancer activity in a far upstream region of the human alpha–fetoprotein gene" *J. Biol. Chem.* 262(10):4812–4818 (1987).

Weinberg et al., "A cell line that supports the growth of a defective early region 4 deletion mutant of human adenovirus type 2" *Proc. Natl. Acad. Sci. USA* 80:5383–5386 (1983).

Wen et al., "Enhancer, repressor, and promoter specificities combine to regulate the rat alpha–fetoprotein gene" *DNA Cell Biol.* 10(7):525–536 (1991).

Wen et al., "A promoter–linked coupling region required for stimulation of alpha–fetoprotein transcription by distant enhancers" *Nucl. Acids Res.* 21(8):1911–1918 (1993).

Wills et al., "Gene therapy for hepatocellular carcinoma: chemosentiveity conferred by adenovirus–mediated transfer of the HSV–1 thymidine kinase gene," *Cancer Gene Ther.* 2:191=197 (1995).

* cited by examiner

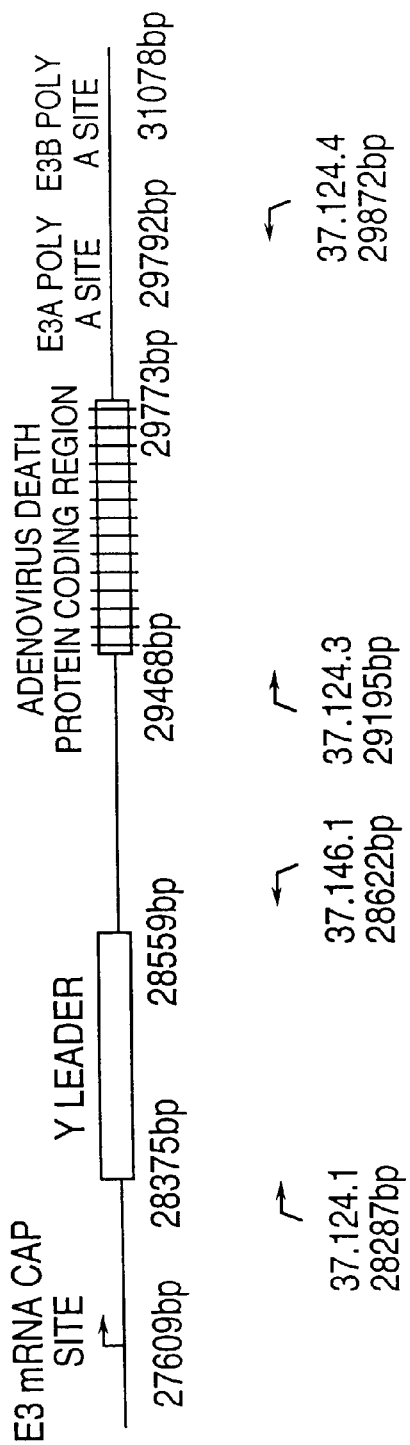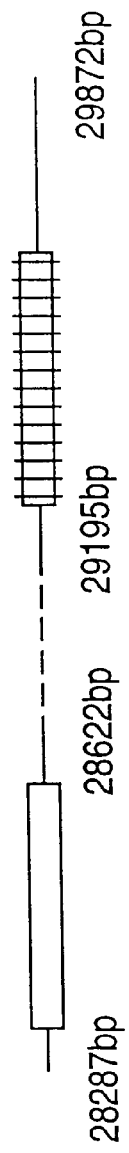
FIG. 5A
FIG. 5B

ADENOVIRUS VECTORS SPECIFIC FOR CELLS EXPRESSING ALPHA-FETOPROTEIN AND METHODS OF USE THEREOF

CROSS-REFERENCE TO RELATED APPLICATIONS

This application is a continuation of U.S. patent application Ser. No. 09/593,308, filed Jun. 13, 2000, now abandoned, which is a continuation of U.S. patent application Ser. No. 09/033,428, filed Mar. 2, 1998, now U.S. Pat. No. 6,254,862, which claims the benefit of U.S. Provisional Application Serial No. 60/039,597, filed Mar. 3, 1997, all of which are incorporated by reference herein in their entirety.

TECHNICAL FIELD

This invention relates to cell transfection using adenoviral vectors. More specifically, it relates to cell-specific replication of adenovirus vectors in cells expressing alpha-fetoprotein, particularly hepatoma cells.

BACKGROUND OF THE INVENTION

In spite of extensive medical research and numerous advances, cancer remains the second leading cause of death in the United States. Hepatocellular carcinoma (HCC or malignant hepatoma) is one of the most common cancers in the world, and is especially problematic in Asia.

Treatment prospects for patients with hepatocellular carcinoma are dim. Even with improvements in therapy and availability of liver transplant, only a minority of patients are cured by removal of the tumor either by resection or transplantation. For the majority of patients, the current treatments remain unsatisfactory, and the prognosis is poor.

Of particular interest is development of more specific, targeted forms of cancer therapy, especially in cancers that are difficult to treat successfully, such as hepatoma. In contrast to conventional cancer therapies, which result in relatively non-specific and often serious toxicity, more specific treatment modalities attempt to inhibit or kill malignant cells selectively while leaving healthy cells intact.

One possible treatment approach for cancers such as hepatoma is gene therapy, whereby a gene of interest is introduced into the malignant cell. The gene of interest may encode a protein which converts into a toxic substance upon treatment with another compound, or an enzyme that converts a prodrug to a drug. For example, introduction of the herpes simplex gene encoding thymidine kinase (HSV-tk) renders cells conditionally sensitive to ganciclovir (GCV). Alternatively, the gene of interest may encode a compound that is directly toxic, such as diphtheria toxin (DT). For these treatments to be rendered specific to cancer cells, the gene of interest can be under control of a transcriptional initiation region that is specifically (i.e., preferentially) activated in the cancer cells. Cell or tissue specific expression can be achieved by using cell-specific enhancers and/or promoters. See generally Huber et al. (1995) Adv. Drug Delivery Reviews 17:279–292.

A variety of viral and non-viral (e.g., liposomes) vehicles, or vectors, have been developed to transfer these genes. Of the viruses, retroviruses, herpes simplex virus, adeno-associated virus, Sindbis virus, poxvirus, and adenoviruses have been proposed for gene transfer with retrovirus vectors or adenovirus vectors being the focus of much current research. Adenoviruses are among the most easily produced and purified, whereas retroviruses are unstable, difficult to produce and to purify, and may integrate into the host genome, raising the possibility of dangerous mutations. Moreover, adenovirus has the advantage of effecting high efficiency of transduction and does not require cell proliferation for efficient transduction of cell. For general background references regarding adenovirus and development of adenoviral vector systems, see Graham et al. (1973) Virology 52:456–467; Takiff et al. (1981) Lancet 11:832–834; Berkner et al. (1983) Nucleic Acid Research 11: 6003–6020; Graham (1984) EMBO J 3:2917–2922; Bett et al. (1993) J. Virology 67:5911–5921; and Bett et al. (1994) Proc. Natl. Acad. Sci. USA 91:8802–8806.

When used as gene transfer vehicles, adenovirus vectors are often designed to be replication-defective and are thus deliberately engineered to fail to replicate in the target cells of interest. In these vehicles, the early adenovirus gene products E1A and/or E1B are deleted and provided in trans by the packaging cell line 293. Graham et al. (1987) J. Gen. Virol 36:59–72; Graham (1977) J. Genetic Virology 68:937–940. The gene to be transduced is commonly inserted into adenovirus in the E1A and E1B region of the virus genome. Bett et al. (1994). Replication-defective adenovirus vectors as vehicles for efficient transduction of genes have been described by, inter alia, Stratford-Perricaudet (1990) Human Gene Therapy 1:241–256; Rosenfeld (1991) Science 252:431–434; Wang et al. (1991) Adv. Exp. Med Biol. 309:61–66; Jaffe et al. (1992) Nat. Gen. 1:372–378; Quantin et al. (1992) Proc. Natl. Acad. Sci. USA 89:2581–2584; Rosenfeld et al. (1992) Cell 68:143–155; Stratford-Perricaudet et al. (1992) J. Clin. Invest. 90:626–630; Le Gal Le Salle et al. (1993) Science 259:988–990 Mastrangeli et al. (1993) J. Clin. Invest. 91:225–234; Ragot et al. (1993) Nature 361:647–650; Hayaski et al. (1994) J. Biol. Chem. 269:23872–23875; Bett et al. (1994).

The virtually exclusive focus in development of adenoviral vectors for gene therapy is use of adenovirus merely as a vehicle for introducing the gene of interest, not as an effector in itself. Replication of adenovirus has been viewed as an undesirable result, largely due to the host immune response. In the treatment of cancer by replication-defective adenoviruses, the host immune response limits the duration of repeat doses at two levels. First, the capsid proteins of the adenovirus delivery vehicle itself are immunogenic. Second, viral late genes are frequently expressed in transduced cells, eliciting cellular immunity. Thus, the ability to repeatedly administer cytokines, tumor suppressor genes, ribozymes, suicide genes, or genes which convert prodrug to an active drug has been limited by the immunogenicity of both the gene transfer vehicle and the viral gene products of the transfer vehicle as well as the transient nature of gene expression. There is a need for vector constructs that are capable of eliminating essentially all cancerous cells in a minimum number of administrations before specific immunological response against the vector prevents further treatment.

A completely separate area of research pertains to the description of tissue-specific regulatory proteins. α-Fetoprotein (AFP) is an oncofetal protein, the expression of which is primarily restricted to developing tissues of endodermal origin (yolk sac, fetal liver, and gut), although the level of its expression varies greatly depending on the tissue and the developmental stage. AFP is of clinical interest because the serum concentration of AFP is elevated in a majority of hepatoma patients, with high levels of AFP found in patients with advanced disease. The serum AFP levels in patients appear to be regulated by AFP expression in hepatocellular carcinoma but not in surrounding normal liver. Thus, the AFP gene appears to be regulated to hepatoma cell-specific expression.

The 5' upstream flanking sequence of the human AFP gene has been shown to confer cell-specific enhancer activity. Watanabe et al. (1987) *J. Biol. Chem.* 262:4812–4818; see also Sakai et al. (1985) *J. Biol. Chem.* 260:5055–5060 (describing cloning the human AFP gene). Canadian pat. appl. no. 2,134,994. An enhancer is a cis-acting transcriptional regulatory element known to play a major role in determination of cell-specificity of gene expression. The enhancer is also typically characterized by its ability to augment transcription over a long distance and relatively independently of orientation and position with respect to its respective gene. A promoter is located immediately 5' (upstream) of the transcription start site and generally includes an AT-rich region called a TATA box.

Several approaches for gene therapy using the cell-specific AFP enhancer to treat hepatoma have been described. Tamaoki and Nakabayashi describe using the AFP transcriptional regulatory regions to drive expression in AFP-producing cells, particularly linking a gene encoding a cancer cell toxin to the AFP transcriptional regulatory region. Canadian pat. app. no. 2,134,994. However, the entire focus of this publication was that of expression of a heterologous toxin gene, such as the gene encoding diphtheria toxin (DT), and adenovirus was only described in terms of a delivery vehicle for this toxin gene. Kaneko et al. and Kanai et al. describe adenovirus-mediated gene therapy of hepatoma using the 5' upstream region of AFP to restrict HSV-tk gene expression to hepatocellular carcinoma cells, followed by treatment with nucleoside analog GCV. *Cancer Res.* 55:5283–5287 (1995); *Hepatology* 22 (4 Part 2): Abstract 158A (1995); *Hepatology* 23:1359–1368 (1996); *Hepatology* 22:Abstract 328 (1995). However, these adenovirus constructs are replication defective, and the entire focus of these publications is using the AFP 5' upstream transcriptional regulatory region to control expression of a non-adenovirus gene. Wills et al.(1995) also describe replication-deficient adenoviral vectors which selectively express HSV-tk. *Cancer Gene Ther.* 2:191–197. Kanai et al. (1996) also reported using the AFP enhancer-promoter to drive expression of the lacZ gene and the *E. coli* cytosine deaminase (CD) gene in addition to the HSV-tk gene. *Gastroenterology (Supp)* 110:A1227. Again, the focus and approach entailed using replication-deficient adenovirus as a therapeutic gene delivery vehicle, not as an agent per se for effecting selective growth inhibition. See also Arbuthnot et al. (1996) (describing using 5' flanking sequences from rat AFP gene). *Human Gene Ther.* 7:1503–1514.

Hepatocellular carcinoma is rarely curable by standard therapies. Thus, it is critical to develop new therapeutic approaches for this disease. The present invention addresses this need by providing adenoviral vectors specific for replication in AFP-producing cells.

All publications cited herein are hereby incorporated by reference in their entirety.

SUMMARY OF THE INVENTION

Replication-competent adenoviral vectors specific, inter alia, for cells expressing AFP and methods for their use are provided. In preferred embodiments, these replication competent-adenovirus vectors comprise one or more of the early and/or late genes essential for adenoviral propagation is under transcriptional control of an AFP transcriptional regulatory element (TRE). A transgene under control of the AFP-TRE cell-specific promoter may also be present. The invention also provides non-naturally-occurring adenoviral vectors comprising the coding sequence for adenovirus death protein (ADP) polypeptide, which may or may not be under cell-specific transcriptional control.

Accordingly, in one aspect, the invention provides an adenovirus vector comprising an adenovirus gene, preferably an adenovirus gene essential for replication, wherein said adenovirus gene is under transcriptional control of an α-fetoprotein transcription response element (AFP-TRE). In one embodiment, an AFP-TRE is human. In one embodiment, an AFP-TRE comprises an AFP-specific promoter and enhancer (i.e., promoter and enhancer from an AFP gene).

In some embodiments, the adenovirus gene essential for replication is an early gene. In another embodiment, the early gene is E1A. In another embodiment, the early gene is E1B. In yet another embodiment, both E1A and E1B are under transcriptional control of an AFP-TRE. In yet another embodiment, E1A, E1B, and E4 are under control of AFP-TREs.

In other embodiments, the adenovirus gene essential for replication is a late gene.

In another embodiment, the AFP-TRE comprises enhancer element A. In another embodiment, the AFP-TRE comprises enhancer element B. In another embodiment, the AFP-TRE comprises enhancer elements A and B.

In another embodiment, the AFP-TRE comprises the nucleotide sequence of SEQ ID NO: 1 or a functionally preserved variant thereof. In another embodiment, the AFP-TRE comprises a nucleotide sequence from about +1 to about +600 of SEQ ID NO: 1. In another embodiment, the AFP-TRE comprises a nucleotide sequence from about +600 to about +827 of SEQ ID NO: 1. In another embodiment, the AFP-TRE comprises a nucleotide sequence from about +1 to about +300 of SEQ ID NO: 1.

In another embodiment, the AFP-TRE comprises the nucleotide sequence of SEQ ID NO: 2 or a functionally preserved variant thereof.

In other embodiments, the adenovirus vector can further comprise a transgene, wherein said transgene is under transcriptional control of an AFP-TRE. In some embodiments, the transgene is a cytotoxic gene.

In other embodiments, the adenovirus vector can further comprise another adenovirus gene, such as an adenovirus gene necessary for replication, under transcriptional control of an AFP-TRE. In other embodiments, yet an another additional adenovirus gene can be under transcriptional control of a third AFP-TRE.

In another aspect, the invention provides a host cell comprising the adenovirus vector(s) described herein.

In another aspect, the invention provides compositions comprising an adenovirus vector(s) described herein, especially an effective amount of an adenovirus vector(s) described herein. The compositions described herein may also further comprise a pharmaceutically acceptable excipient.

In another aspect, the invention provides kits which contain an adenoviral vector(s) described herein.

Another embodiment of the invention is an adenovirus which replicates preferentially in cells which allow an AFP-TRE to function, especially mammalian cells expressing AFP or capable of expressing AFP.

In another aspect, methods are provided for propagating an adenovirus specific for cells which allow an AFP-TRE to function, such as cells (particularly mammalian cells) expressing AFP, said method comprising combining an adenovirus vector(s) described herein with cells which allow an AFP-TRE to function, whereby said adenovirus is propagated.

In another aspect, methods are provided for conferring selective cytotoxicity in cells which allow an AFP-TRE to function, such as cells expressing AFP, comprising contacting the AFP-expressing cells with an adenovirus vector(s) described herein, wherein the adenovirus vector enters the cell.

In another aspect, methods are provided for detecting cells which allow an AFP-TRE to function, comprising contacting cells of a biological sample with an adenovirus vector(s) described herein and detecting AFP-TRE mediated expression, if any.

In another aspect, methods are provided for detecting cells expressing α-fetoprotein in a biological sample, comprising contacting cells of a biological sample with an adenovirus vector(s) described herein, and detecting replication of the adenovirus vector, if any.

In another aspect, methods of treatment are provided wherein an adenoviral vector(s) described herein is administered to an individual.

In another aspect, the invention provides a non-naturally occurring adenoviral vector comprising a polynucleotide encoding adenovirus death protein (ADP) polypeptide. In some embodiments, the ADP coding sequence is under transcriptional control of a cell-specific TRE, such as an AFP-TRE or a prostate-cell specific TRE.

BRIEF DESCRIPTION OF THE DRAWINGS

FIG. 1A shows some of the features of the promoter/enhancer region, including: enhancer domains A and B; distal silencer (Sd); proximal silencer (Sp); and glucocorticoid response element (GRE). Numbers indicate nucleotide positions relative to the transcription start site (indicated by bent arrow).

FIG. 2(A) is a schematic of CN236, a luciferase reporter plasmid construct that was used to assess transcriptional activity of an AFP-TRE.

FIGS. 5A and B are schematic depictions an adenovirus death protein (ADP) cassette for insertion into Ad. Arrows underneath FIG. 5A indicate positions of primers. FIG. 5B depicts the annealed fragment containing the Y leader sequence and the ADP coding sequence.

In FIG. 6(A), the left panel shows Huh-7 (AFP+) cells; the right panel shows Dld-1 (AFP−) cells.

FIG. 7(A)) and non-AFP producing (Sk-Hep-1, FIG. 7(B); Dld-1, FIG. 7(C)) cells.

FIG. 10(A) depicts measuring tumor volume over a period of 43 days (six weeks). In FIG. 10(B), single intratumoral administration of CN733 ("B") was compared to five consecutive daily doses of CN733 ("J").

MODES FOR CARRYING OUT THE INVENTION

Figure 1A:
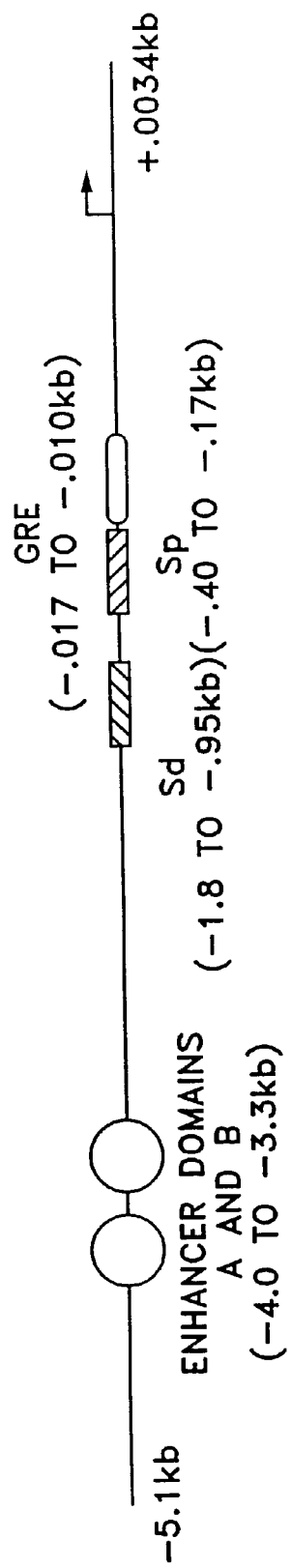
FIG. 1A depicts a schematic map of the human AFP enhancer and promoter region (not to scale).

We have discovered and constructed replication competent-adenovirus vectors which can preferentially replicate in cells that express α-fetoprotein (AFP) and developed methods using these adenovirus vectors. The adenovirus vectors of this invention comprise at least one adenovirus gene, preferably an adenovirus gene that contributes to cytotoxicity, preferably an adenovirus gene necessary for adenoviral replication, preferably at least one early gene, under the transcriptional control of a transcriptional response element (TRE) specifically regulated by binding of transcriptional factor(s) and/or co-factor(s) necessary for transcription of the AFP gene (AFP-TRE). By providing for cell-specific transcription of at least one. adenovirus gene required for replication, the invention provides adenovirus vectors that can be used for specific cytotoxic effects due to selective replication. This is especially useful in the cancer context, in which targeted cell killing is desirable. The vectors can also be useful for detecting the presence of AFP-producing cells in, for example, an appropriate biological (such as clinical) sample. Further, the adenovirus vector(s) can optionally selectively produce one or more proteins of interest in a target cell by using an AFP-TRE.

We have found that adenovirus vectors of the invention replicate preferentially in AFP-producing cells (i.e., at a significantly higher yield than in non-AFP producing cells). This replication preference is indicated by comparing the level of replication (i.e., titer) in cells producing AFP to the level of replication in cells not producing AFP. The replication preference is even more significant, as the adenovirus vectors of the invention actually replicate at a significantly lower rate in non-AFP producing cells than wild type virus. Comparison of the titer of an AFP+ cell type to the titer of an AFP− cell type provides a key indication that the overall replication preference is enhanced due to depressed replication in AFP− cells as well as the replication in AFP+ cells when compared to wild type adenovirus. This aspect is particularly significant and useful in the cancer context, in which it is desirable to minimize cytotoxic damage to non-target (i.e., non-cancerous cells). Example 1 provides a more detailed description of these experiments and findings.

Further, we have found that an adenovirus vector of the invention significantly retarded growth of a HepG2 xenograft in nude mice (Example 5). Thus, the invention uses and takes advantage of what has been considered an undesirable aspect of adenoviral vectors, namely, their replication and possibly concomitant immunogenicity. The probability of runaway infection is significantly reduced due to the cell-specific requirements for viral replication. Without wishing to be bound by any particular theory, the inventors note that production of adenovirus proteins can serve to activate and/or stimulate the immune system, generally and/or specifically toward target cells producing adenoviral proteins, which can be an important consideration in the cancer context, where patients are often moderately to severely immunocompromised.

We have also discovered that inclusion of a coding sequence for ADP significantly enhances the extent of cytotoxicity, cell killing, and virus production when compared to an adenoviral vector lacking this sequence. Accordingly, non-naturally occurring adenovirus vectors containing a coding sequence for an ADP polypeptide are included and described herein. The ADP coding sequence may or may not be under transcriptional control of a cell-specific TRE (i.e., under selective transcriptional control), such as an AFP-TRE.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sanbrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

For techniques related to adenovirus, see, *inter alia*, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

As used herein, an "α-fetoprotein transcriptional response element", or "AFP-TRE" is polynucleotide sequence, preferably a DNA sequence, which increases transcription of an operably linked polynucleotide sequence in a host cell that allows an AFP-TRE to function, such as a host cell that expresses AFP. According to published reports, the AFP-TRE is responsive to cellular proteins (transcription factors and/or co-factor(s)) associated with APP-producing cells, such as AFP-binding protein (see, for example, U.S. Pat. No. 5,302,698) and comprises at least a portion of an AFP promoter and/or an AFP enhancer. Methods are described herein for measuring the activity of an AFP-TRE and thus for determining whether a given cell allows an AFP-TRE to function.

As described in more detail herein, an AFP-TRE can comprise any number of configurations, including, but not limited to, an AFP promoter; an AFP enhancer; an AFP promoter and an AFP enhancer; an AFP promoter and a heterologous enhancer; a heterologous promoter and an AFP enhancer; and multimers of the foregoing. The promoter and enhancer components of an AFP-TRE may be in any orientation and/or distance from the coding sequence of interest, as long as the desired AFP cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operably linked to)-the AFP-TRE. As discussed herein, an AFP-TRE can be of varying lengths, and of varying sequence composition. By "transcriptional activation" or an "increase in transcription," it is intended that transcription is increased above basal levels in the target cell (i.e., AFP-producing cell) by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Basal levels are generally the level of activity (if any) in a non-AFP producing cell, or the level of activity (if any) of a reporter construct lacking an AFP-TRE as tested in an AFP-producing cell. Optionally, a transcriptional terminator or transcriptional "silencer" can be placed upstream of the AFP-TRE, thus preventing unwanted read-through transcription of the coding segment under transcriptional control of the PB-TRE. Also, optionally, the endogenous promoter of the coding segment to be placed under transcriptional control of the PB-TRE can be deleted.

A "functionally-preserved" variant of an AFP-TRE is an AFP-TRE which differs from another AFP-TRE, but still retains ability to increase transcription of an operably linked polynucleotide, especially AFP cell-specific transcription activity. The difference in an AFP-TRE can be due to differences in linear sequence, arising from, for example, single or multiple base mutation(s), addition(s), deletion(s), and/or modification(s) of the bases. The difference can also arise from changes in the sugar(s), and/or linkage(s) between the bases of an AFP-TRE.

A "cell-specific TRE" is preferentially functional in a specific type of cell relative to other types of cells of different functionality. A cell-specific TRE may or may not be tumor cell specific.

As used herein, the term "target cell-specific" is intended to mean that the TRE sequences to which a gene essential for replication of an adenoviral vector is operably linked, or to which a transgene is operably linked, functions specifically in that target cell so that replication proceeds in that target cell, or so that a transgene polynucleotide is expressed in that target cell. This can occur by virtue of the presence in that target cell, and not in non-target cells, of transcription factors that activate transcription driven by the operably linked transcriptional control sequences. It can also occur by virtue of the absence of transcription inhibiting factors that normally occur in non-target cells and prevent transcription driven by the operably linked transcriptional control sequences. The term "target cell-specific", as used herein, is intended to include cell type specificity, tissue specificity, as well as specificity for a cancerous state of a given target cell. In the latter case, specificity for a cancerous state of a normal cell is in comparison to a normal, non-cancerous counterpart.

An "adenovirus vector" or "adenoviral vector" (used interchangeably) is a term well understood in the art and generally comprises a polynucleotide comprising all or a portion of an adenovirus genome. For purposes of the present invention, an adenovirus vector contains an AFP-TRE operably linked to a polynucleotide. The operably linked polynucleotide can be an adenovirus gene or a heterologous gene. An adenoviral vector construct of this invention may be in any of several-forms, including, but not limited to, naked DNA, DNA encapsulated in an adenovirus coat, DNA packaged in another viral or viral-like form (such as herpes simplex, and AAV), encapsulated in liposomes, complexed with polylysine, complexed with synthetic polycationic molecules, conjugated with transferrin, and complexed with compounds such as PEG to immunologically "mask" the molecule and/or increase half-life, and conjugated to a nonviral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothiate linkage can be used in place of a phosphodiester linkage. Braun et al. (1988) *J. Immunol.* 141: 2084–9; Latimer et al. (1995) *Mol. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example, those described in *Current Protocols in Molecular Biology* (Ausubel et al., eds., 1987), Supp. 30, section 7.7.18, Table 7.7.1. A preferred alignment program is ALIGN Plus (Scientific and Educational Software, Pennsylvania).

"Under transcriptional control" is a term well-understood in the art and indicates that transcription of a polynucleotide sequence, usually a DNA sequence, depends on its being operably (operatively) linked to an element which contributes to the initiation of, or promotes, transcription. As noted below, "operably linked" refers to a juxtaposition wherein the elements are in an arrangement allowing them to function.

The terms "polypeptide", "oligopeptide", "peptide" and "protein" are used interchangeably herein to refer to polymers of amino acids of any length. The polymer may be linear or branched, it may comprise modified amino acids, it may be interrupted by non-amino acids, and it may be assembled into a complex of more than one polypeptide chain. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In the context of polypeptides, a "linear sequence" or a "sequence" is an order of amino acids in a polypeptide in an N-terminal to C-terminal direction in which residues that neighbor each other in the sequence are contiguous in the primary structure of the polypeptide. A "partial sequence" is a linear sequence of part of a polypeptide which is known to comprise additional residues in one or both directions.

A polypeptide "fragment" (also called a "region") of ADP (or a "ADP fragment" or "ADP region") is a polypeptide comprising an amino acid sequence of ADP that has at least 5 contiguous amino acids of a sequence of ADP, more preferably at least 10 contiguous amino acids, more preferably at least about 15 contiguous amino acids, even more preferably at least about 25 contiguous amino acids, even more preferably at least about 30 contiguous amino acids, even more preferably at least about 40 contiguous amino acids. An ADP fragment may be characterized as having any of the functions attributed to ADP, including those described herein.

"Replication" and "propagation" are used interchangeably and refer to the ability of an adenovirus vector of the invention to reproduce, or proliferate. This term is well understood in the art. For purposes of this invention, replication involves production of adenovirus proteins and is generally directed to reproduction of adenovirus. Replication can be measured using assays standard in the art and described herein, such as a burst assay, plaque assay, or a one-step growth curve assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

As used herein, "cytotoxicity" is a term well understood in the art and refers to a state in which one or more of a cell's usual biochemical or biological functions are aberrantly compromised (i.e., inhibited or elevated). These activities include, but are not limited to, metabolism; cellular replication; DNA replication; transcription; translation; and uptake of molecules. "Cytotoxicity" includes cell death and/or cytolysis. Assays are known in the art which indicate cytotoxicity, such as dye exclusion, $^3$H-thymidine uptake, and plaque assays. The term "selective cytotoxicity", as used herein, refers to the cytotoxicity conferred by an adenovirus vector of the present invention on a cell which allows an AFP-TRE to function when compared to the cytotoxicity conferred by the adenovirus on a cell which does not allow an AFP-TRE to function. Such cytotoxicity may be measured, for example, by plaque assays, or the reduction or stabilization in size of a tumor comprising target cells, or the reduction or stabilization of serum levels of a marker characteristic of the tumor cells or a tissue-specific marker, e.g., a cancer marker such as AFP or prostate-specific antigen.

A "heterologous gene" or "transgene" is any gene that is not present in wild-type adenovirus. Preferably, the transgene will also not be expressed or present in the target cell prior to introduction by the adenovirus vector. Examples of preferred transgenes are provided below.

A "heterologous" promoter or enhancer is one which is not associated with or derived from an AFP gene 5' flanking sequence. Examples of a heterologous promoter or enhancer are the albumin promoter or enhancer and other viral promoters and enhancers, such as SV40.

An "endogenous" promoter, enhancer, or TRE is native to or derived from adenovirus.

The term "operably linked" relates to the orientation of polynucleotide elements in a functional relationship. A TRE is operably linked to a coding segment if the TRE promotes transcription of the coding sequence. Operably linked means that the DNA sequences being linked are generally contiguous and, where necessary to join two protein coding regions, contiguous and in the same reading frame. However, since enhancers generally function when separated from the promoter by several kilobases and intronic sequences may be of variable length, some polynucleotide elements may be operably linked but not contiguous.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

A "target cell" is any cell that allows an AFP-TRE to function. Preferably, a target cell is a mammalian cell, preferably a mammalian AFP-expressing cell, more preferably, a human cell expressing AFP.

As used herein, "neoplastic cells," "neoplasia," "tumor," "tumor cells," "cancer" and "cancer cells" (used interchangably) refer to cells which exhibit relatively autonomous growth, so that they exhibit an aberrant growth phenotype characterized by a significant loss of control of cell proliferation. Neoplastic cells can be benign or malignant.

As used herein, "a cell which allows an AFP-TRE to function", a cell in which the function of an AFP-TRE is "sufficiently preserved", "a cell in which an AFP-TRE is functional", or the like is a cell in which an AFP-TRE, when operably linked to, for example, a reporter gene, increases expression of the reporter gene at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to 500-fold, even more preferably at least about 1000-fold, when compared to the expression of the same reporter gene when not linked to the AFP-TRE. Methods for measuring levels (whether relative or absolute) of expression are known in the art and are described herein.

A "non-naturally occurring" or "recombinant" adenoviral vector are used interchangably and mean that an adenoviral vector which either does not occur in nature or contains polynucleotide elements (or components) which are in an arrangement not found in nature. As discussed herein, in the context of adenoviral vectors containing coding sequence(s) for ADP, the term encompasses those adenoviral vectors that are non-naturally occurring or recombinant due to manipulations involving ADP sequences and/or those manipulations not involving ADP sequences. For example, a non-naturally occurring adenoviral vector comprising an ADP coding sequence may have contained the ADP coding sequence prior to any manipulation but has been rendered non-naturally occurring due to insertion and/or deletion of other sequence element(s). For example, such an adenoviral vector may comprise a cell specific TRE regulating transcription of an early gene in an adenoviral vector that also contains and ADP encoding sequence. As another example, a non-naturally occurring adenoviral vector may arise by adding an ADP encoding sequence to an adenoviral vector which did not contain such a sequence (see Example 5).

An "ADP coding sequence" is a polynucleotide that encodes ADP or a functional fragment thereof. In the context of ADP, a "functional fragment" of ADP is one that exhibits cytotoxic activity, especially cell lysis, with respect to adenoviral replication. Ways to measure cytotoxic activity are known in the art and are described herein.

A polynucleotide that "encodes" an ADP polypeptide is one that can be transcribed and/or translated to produce an ADP polypeptide or a fragment thereof. The anti-sense strand of such a polynucleotide is also said to encode the sequence.

An "ADP polypeptide" is a polypeptide containing at least a portion, or region, of the amino acid sequence of an ADP (see, for example, SEQ ID NO: 23), and which displays a function associated with ADP, particularly cytotoxicity, more particularly, cell lysis. As discussed herein, these functions can be measured using techniques known in the art. It is understood that certain sequence variations may be used, due to, for example, conservative amino acid substitutions, which may provide ADP polypeptides.

A polynucleotide or polypeptide sequence that is "depicted in" a SEQ ID NO means that the sequence is present as an identical contiguous sequence in the SEQ ID NO. The term encompasses portions, or regions of the SEQ ID NO as well as the entire sequence contained within the SEQ ID NO.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, and pets.

An "effective amount" is an amount sufficient to effect beneficial or desired clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to riot administering adenoviral vectors of the present invention.

Adenoviral Vectors Having Replication Specificity for AFP-producing Cells

The present invention provides adenoviral vector constructs which comprise an adenoviral gene under transcriptional control of an AFP-TRE. Preferably, the advenovirus gene contributes to cytotoxicity (whether direct and/or indirect), more preferably one that contributes to or causes cell death, even more preferably is essential for advenoviral replication. Examples of a gene that contributes to cytotoxicity include, but are not limited to, advenovirus death protein (ADP; discussed below). When the adenovirus vector(s) is selectively (i.e., preferentially) replication competent for propagation in target cells expressing AFP, these cells will be preferentially killed upon adenoviral proliferation. By combining the adenovirus vector(s) with a mixture of malignant and normal liver cells, for example, in vitro or in vivo, the adenovirus vector(s) will preferentially replicate in the target malignant liver cells. Once the target cells are destroyed due to selective cytotoxic and/or cytolytic replication, the adenovirus vector replication is significantly reduced, thus lessening the probability of runaway infection and undesirable bystander effects. In vitro cultures may be retained to monitor the mixture (such as, for example, a biopsy or other appropriate biological sample) for occurrence (i.e., presence) and/or recurrence of the target cell, e.g., an AFP-producing neoplastic cell. To further ensure cytotoxicity, one or more transgenes having a cytotoxic effect may also be present and under selective transcriptional control. In this embodiment, one may provide higher confidence that the target cells will be destroyed. Additionally, or alternatively, an adenovirus gene that contributes to cytotoxicity and/or cell death (such as ADP) may be included in the adenoviral vector, either free of, or under, selective transcriptional control.

The AFP-TREs used in this invention are derived from mammalian cells, including but not limited to, human, rat, and mouse. Rodent and human AFP 5' flanking sequences have been described in the literature and are thus made available for practice of this invention and need not be described in detail herein. Rat AFP 5' flanking sequences have been described and characterized. Wen et al. (1991) *DNA Cell Biol.* 10:525–536; Wen et al. (1993) *Nucl. Acids Res.* 21:1911–1918. The rat AFP 5' flanking region contains three upstream enhancers denoted complex 1 (from −2800 to −2400), complex 2 (from −4500 to −3500), and complex 3 (from −7000 to 4900). The promoter region encompasses −250 to −1; the promoter element from −178 to −155 is required if the enhancers are distant but is dispensable if the enhancer(s) is closer. Wen et al. (1991 and 1993). Groupp et al. (1994) report activity of complex 3 (on a 344 bp HincII fragment), the most distal enhancer element. *J. Biol. Chem.* 269:22178–22187. Arbuthnot et al. (1996) showed activity of sequences −3127 to +102, which encompass the most proximal enhancer and promoter (and region homologous to the mouse silencer sequence) in human hepatoma cell lines HuH7, Hep 3B, and HepG2.

Mouse 5' flanking AFP sequences have been described and characterized. Ghebranious et al. (1995) *Mol. Reprod. Devel.* 42:1–6. Like rat, mouse 5' flanking AFP sequences contain three separate enhancer elements. A silencer, or element associated with shut off in the adult liver, is found between −838 and −250. Emerson et al. (1992) *Devel. Dynam.* 195:55–66.

Preferably, the AFP-TRE is human. The cloning and characterization of AFP-specific enhancer activity is described in Watanabe et al. (1987). The entire 5' AFP flanking region (containing the promoter, putative silencer, and enhancer elements) is contained within approximately 5 kb upstream from the transcription start site. The AFP enhancer region in human is located between about −3954 and about −3335, relative to the transcription start (CAP) site of the AFP gene. The human AFP promoter encompasses a region from about −174 to about +29. Ido et al. (1995) describe a 259 bp promoter fragment (−230+29) that is specific for HCC. *Cancer Res.* 55:3105–3109. The AFP enhancer contains two regions, denoted A and B, located between −3954 and −3335 relative to the transcription start site. The promoter region contains typical TATA and CAAT boxes. Preferably, the AFP-TRE contains at least one enhancer region. More preferably, the AFP-TRE contains both enhancer regions.

Kaneko et al. (1995) have used a 4.9 kb HindIII to HindIII fragment. Kanai et al. (1995 and 1996) have shown activity on a shorter fragment which contained a 0.2 kb (BglII to HindIII) promoter segment and a segment containing enhancers A and B (−4.0 to −3.3 kb; ApaI to BglII).

Figure 1B:
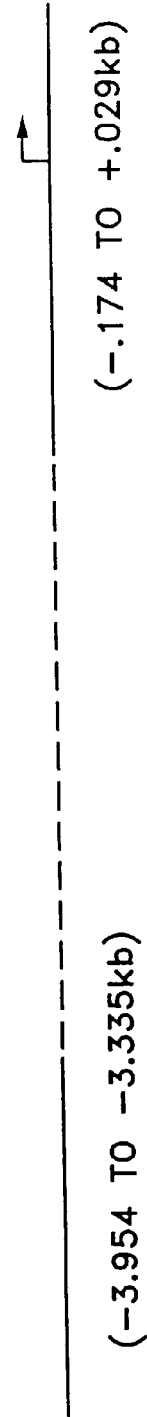
FIG. 1B is a schematic depicting two 5' AFP regions used in constructing an AFP-TRE (described in Example 1).
Figure 2A:
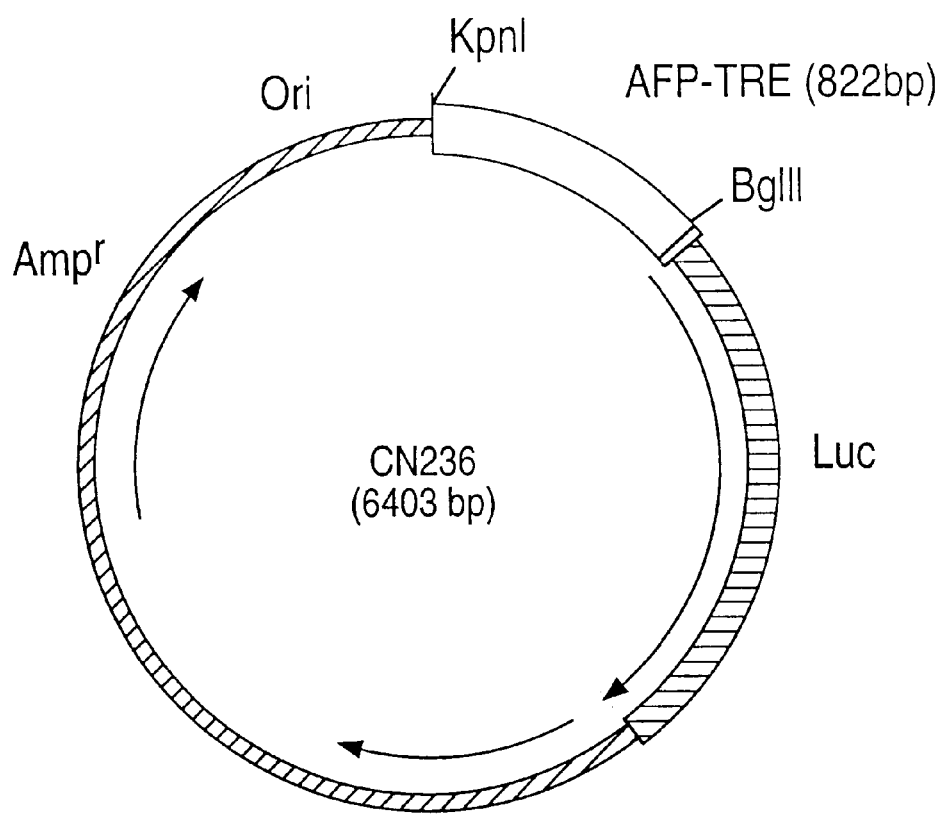
FIGS. 2(A) and (B) summarize a reporter assay experiment for an AFP-TRE.
Figure 2B:
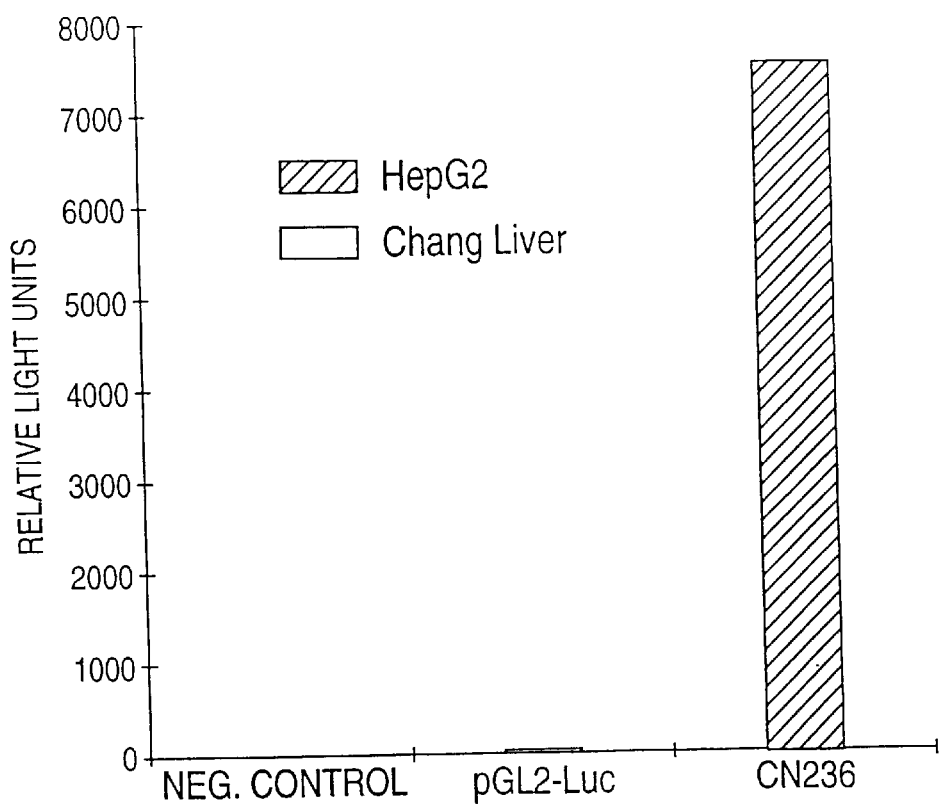
FIG. 2(B) is a bar graph depicting a luciferase reporter assay for an 800 bp AFT-TRE. The 800 bp fragment was tested for its ability to drive expression of luciferase in Hep3B cells which produce AFP. pGL2-Luc is a negative control in which the luciferase gene is not linked to AFP-TRE sequences.
Figure 3:
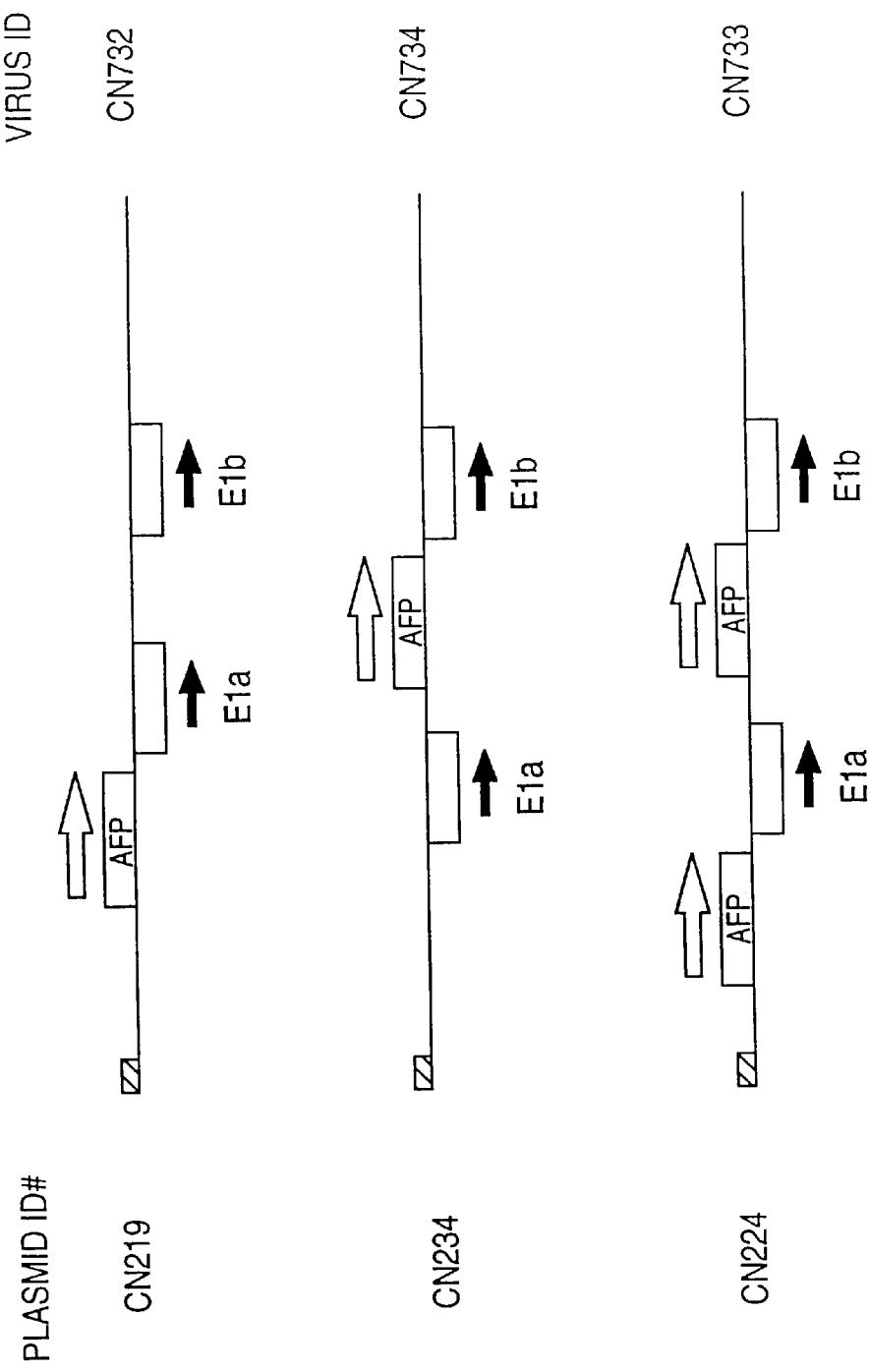
FIG. 3 is a schematic depicting various adenoviral vector construct as described in Example 1.

In one embodiment, the AFP-TRE comprises an approximately 0.6 kb enhancer region (from −3954 to −3335) and a 0.2 kb promoter region (−174 to +29), both of which are specific for AFP-producing cells as shown in FIG. 1B. Juxtaposition of these two genetic elements yields a fully functional AFP-TRE (Example 1). Accordingly, the invention also includes an adenovirus vector in which the AFP-TRE comprises SEQ ID NO: 1 (i.e., the sequence of SEQ ID NO: 1).

In another embodiment, the AFP-TRE comprises the sequence from about +1 to about +600 of SEQ ID NO: 1. This embodiment thus comprises enhancer regions A and B. In another embodiment, the AFP-TRE comprises the sequence from about +600 to about +827 of SEQ ID NO: 1, thus comprising the AFP promoter. The enhancer region may be further subdivided (regions A and B); thus, further embodiments include: (a) an AFP-TRE that comprises nucleotide sequence from about +1 to about +300 of SEQ ID NO: 1; (b) an AFP-TRE that comprises nucleotide sequence from about +300 to about +600 of SEQ ID NO: 1.

In another embodiment, the AFP-TRE contains the entire 5.1 kb 5' flanking sequence (SEQ ID NO: 2).

An AFP-TRE can also comprise multimers. For example, an AFP-TRE can comprise a tandem series of at least two, at least three, at least four, or at least five AFP promoter fragments. Alternatively, an AFP-TRE could have one or more AFP promoter regions along with one or more AFP enhancer regions. These multimers may also contain heterologous promoter and/or enhancer sequences.

An AFP-TRE may or may not lack a silencer. The presence of a silencer (i.e., a negative regulatory element) may assist in shutting off transcription (and thus replication) in non-permissive (i.e., non-AFP-producing) cells. Thus, presence of a silencer may confer enhanced cell-specific replication by more effectively preventing adenoviral vector replication in non-target cells. Alternatively, lack of a silencer may assist in effecting replication in target cells, thus conferring enhanced cell-specific replication due to more effective replication in target cells. The 5' flanking region of the AFP gene has been shown to contain two silencer elements, from −1822 to −951 (distal element) and from −402 to −169 (proximal element). Nakabayashi et al. (1991) *Mol. Cell. Biol.* 11:5885–5893. Kanai et al. (1995) have reported the activity of a fragment lacking the silencer is higher than reported activities for the approximately 5.0 kb native 5' flanking region.

As is readily appreciated by one skilled in the art, an AFP-TRE is a polynucleotide sequence, and, as such, can exhibit function over a variety of sequence permutations. Methods of nucleotide substitution, addition, and deletion are known in the art, and readily available functional assays (such as the CAT or luciferase reporter gene assay) allow one of ordinary skill to determine whether a sequence variant exhibits requisite cell-specific transcription function. Hence, the invention also includes functionally-preserved variants of the nucleic acid sequences disclosed herein, which include nucleic acid substitutions, additions, and/or deletions. While not wishing to be bound by a single theory, the inventors note that it is possible that certain modifications will result in modulated resultant expression levels, including enhanced expression levels. Achievement of modulated resultant expression levels, preferably enhanced expression levels, may be especially desirable in the case of certain, more aggressive forms of hepatoma, or when a more rapid and/or aggressive pattern of cell killing is warranted (due to an immunocompromised condition of the individual, for example).

As an example of how AFP-TRE activity can be determined, a polynucleotide sequence or set of such sequences can be generated using methods known in the art, such as chemical synthesis, site-directed mutagenesis, PCR, and/or recombinant methods. The sequence(s) to be tested is inserted into a vector containing an appropriate reporter gene, including, but not limited to, chloramphenicol acetyl transferase (CAT), β-galactosidase (encoded by the lacZ gene), luciferase (encoded by the luc gene), green fluorescent protein, alkaline phosphatase, and horse radish peroxidase. Such vectors and assays are readily available, from, inter alia, commercial sources. Plasmids thus constructed are transfected into a suitable host cell to test for expression of the reporter gene as controlled by the putative AFP-TRE using transfection methods known in the art, such as calcium phosphate precipitation, electroporation, liposomes (lipofection), and DEAE-dextran. Suitable host cells include any cell type that produces AFP, including but not limited to, Hep3B, Hep G2, HuH7, HuH1/C12 and AFP-SK-Hep-1. Non-AFP producing cells, such as LNCaP, HBL-100, Chang liver cells, MCF-7, HLF, HLE, 3T3, and HeLa are used as a control. Results are obtained by measuring the level of expression of the reporter gene using standard assays. Comparison of expression between AFP-producing cells and control indicates presence or absence of transcriptional activation. Example 2 describes an experiment in which an 800 bp putative AFP-TRE (a 0.6 kb enhancer region fused to a 0.2 kb promoter region, as described above) was tested using a luciferase reporter assay.

By transcriptional increase or activation, it is intended that transcription is increased above basal levels in the target cell (i.e., AFP-producing cell) by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Comparisons between or among various AFP-TREs can be assessed by measuring and comparing levels of expression within a single AFP-producing cell line. It is understood that absolute transcriptional activity of an AFP-TRE will depend on several factors, such as the nature of the target cell, delivery mode and form of the AFP-TRE, and the coding sequence that is to be selectively transitionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the cytomegalovirus (CMV) immediate early promoter. This analysis can also indicate negative regulatory regions, i.e., silencers.

Alternatively a putative AFP-TRE can be assessed for its ability to confer adenoviral replication preference for cells expressing AFP. For this assay, constructs containing an adenovirus gene essential to replication operatively linked to a putative AFP-TRE are transfected into cells that express AFP. Viral replication in those cells is compared, for example, to viral replication by the construct in cells not producing AFP. A more detailed description of this kind of assay is in Example 1.

It is understood that, to practice this invention, it is not necessary to use AFP-TREs having maximum activity, or having minimum size. The requisite degree of activity is determined, inter alia, by the anticipated use and desired result. For example, if an adenoviral vector of the invention is used to monitor cells for AFP-producing activity, it is possible that less than maximal degree of responsiveness by an AFP-TRE will suffice to indicate qualitatively the presence of such cells. Similarly, if used for treatment or palliation of a disease state, less-than-maximal responsiveness may be sufficient for the desired result, if, for example, the AFP-producing cells are not especially virulent and/or the extent of disease is relatively confined.

The size of AFP-TREs will be determined in part by the capacity of the adenoviral vector, which in turn depends upon the contemplated form of the vector (see below). Generally a minimal size is preferred, as this provides potential room for insertion of other sequences which may be desirable, such as transgenes (discussed below) or additional regulatory sequences. However, if no additional sequences are contemplated, or if, for example, an adenoviral vector will be maintained and delivered free of any viral packaging constraints, a larger AFP-TRE may be used as long as the resultant adenoviral vector is rendered replication competent.

If no adenovirus sequences have been deleted, an adenoviral vector can be packaged with extra sequences totaling up to about 5% of the genome size, or approximately 1.8 kb. If non-essential sequences are removed from the adenovirus genome, then an additional 4.6 kb of insert can be tolerated (i.e., a total of about 1.8 kb plus 4.6 kb, which is about 6.4 kb). Examples of non-essential adenoviral sequences that can be deleted are E3 and E4 (as long as E4 ORF6 is maintained).

Because AFP-specific transcriptional activity has been shown in a 5.1 kb 5' flanking fragment, and AFP-TRE can be at least as large as about 5.0 kb. Preferably, an AFP-TRE will comprise a polynucleotide sequence of about 2.5 kb, more preferably about 1 kb, more preferably about 0.8 kb, even more preferably about 0.5 kb, even more preferably about 0.3 kb (which is the approximate size of one of the AFP enhancer elements).

Various replication-competent adenovirus vectors can be made according to the present invention in which a single or multiple adenovirus gene(s) is under control of an AFP-TRE. For example, an AFP-TRE may be introduced into an adenovirus vector immediately upstream of and operably linked to a replication gene, e.g., an early gene such as E1A, E1B or E4, or a late gene such as L1, L2, L3, L4, or L5. In some embodiments, the adenoviral vectors comprise an E1A gene under transcriptional control of an AFP-TRE. In other embodiments, the adenoviral vectors comprise an E1B gene under transcriptional control of an AFP-TRE. In other embodiments, the adenoviral vectors comprise an E4 gene under transcriptional control of an AFP-TRE. In other embodiments, various combinations and permutations of the above may be practiced. For example, in some embodiments, the adenoviral vectors comprise an E1A gene under transcriptional control of an AFP-TRE, and E1B gene under transcriptional control of an AFP-TRE (i.e., a "double" AFP-TRE construct"). In other embodiments, the adenoviral vectors comprise an E1A gene under transcriptional control of an AFP-TRE, an E1B gene under transcriptional control of a second AFP-TRE, and an E4 gene under transcriptional control of a third AFP-TRE. "First", "second", "third", and the like AFP-TREs in this context means that separate AFP-TREs drive each respective gene.

The AFP-TREs used may or may not have the same sequence composition. However, as described elsewhere, it is also possible to have a single AFP-TRE regulate transcription of more than one adenovirus gene.

Figure 4:
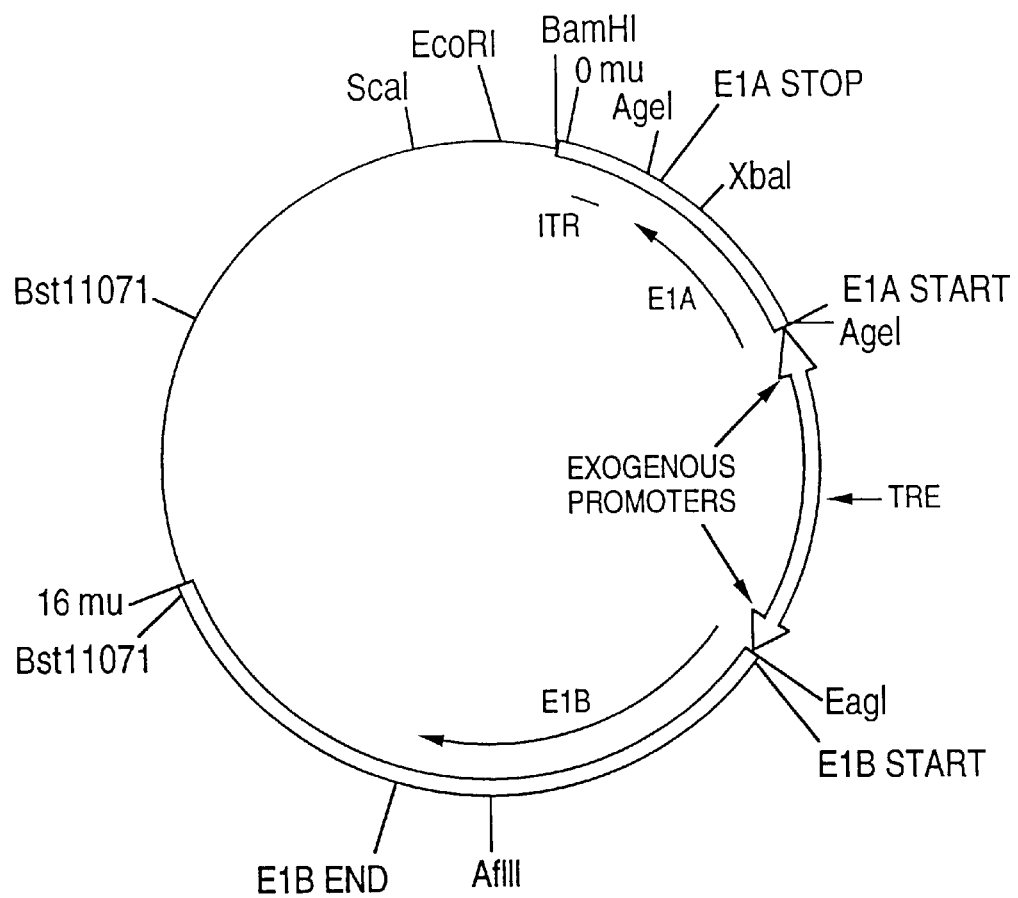
FIG. 4 is a schematic depiction of an adenoviral vector in which E1A and E1B are under control of an AFP-TRE, with E1A and E1B in opposite orientations.

In one embodiment, E1A and E1B are under control of one or more AFP-TREs by making the following construct. In wild-type adenovirus, E1A and E1B are in tandem orientation. A fragment containing the coding region of E1A through the E1B promoter is excised from the adenovirus genome and reinserted in the opposite orientation (FIG. 4). In this configuration, the E1A and E1B promoters are next to each other, followed by E1A coding segment in opposite orientation (so that neither the E1A or E1B promoters are operably linked to E1A), followed by E1B in opposite orientation with respect to E1A. An AFP-TRE(s) can be inserted between E1A and E1B coding regions, (which are in opposite orientation), so that these regions are under control of the TRE(s). Appropriate promoter sequences are inserted proximal to the E1A and E1B region as shown in FIG. 4. Thus, an AFP-TRE may drive both E1A and E1B. Such a configuration may prevent, for example, possible loop-out events that may occur if two AFP-TREs were inserted in intact (native) Ad genome, one each 5' of the coding regions of E1A and E1B. By introducing a polycloning site between E1A and E1B, other types of AFP, or liver-specific TREs can be inserted, or other cell-specific regulatory elements, preferably those associated with a disease state, such as neoplasm. Thus, this construct may find general use for cell-specific, temporal, or other means of control of adenovirus genes E1A and E1B, thereby providing a convenient and powerful way to render adenoviral replication dependent upon a chosen transcriptional parameter.

Various other replication-competent adenovirus vectors can be made according to the present invention in which, in addition to having a single or multiple adenovirus gene(s) are under control of an AFP-TRE, reporter gene(s) are under control of an AFP-TRE.

For example, an AFP-TRE may be introduced into an adenovirus vector immediately upstream of and operably linked to an early gene such as E1A or E1B, and this construct may also contain a second AFP-TRE driving expression of a reporter gene. The reporter gene can encode a reporter protein, including, but not limited to, chloramphenicol acetyl transferase (CAT), β-galactosidase (encoded by the lacZ gene), luciferase, alkaline phosphatase, green fluorescent protein, and horse radish peroxidase. For detection of a putative prostate cell(s) in a biological sample, the biological sample may be treated with modified adenoviruses in which a reporter gene (e.g., luciferase) is under control of an AFP-TRE. The AFP-TRE will be transcriptionally active in cells which allow the AFP-TRE to function (such as AFP-expressing cells), and luciferase will be produced. This production allows detection of cells producing androgen receptor in, for example, a human host or a biological sample. Alternatively, an adenovirus vector can be constructed in which the gene encoding a product conditionally required for survival (e.g., an antibiotic resistance marker) is under control of an AFP-TRE. When this adenovirus vector is introduced into a biological sample, cells which allow an AFP-TRE to function, such as AFP-expressing cells, will become antibiotic resistant. An antibiotic can then be introduced into the medium to kill non-androgen receptor producing cells.

In order to minimize non-specific replication, endogenous (i.e., adenovirus) TRE's should preferably be removed. This would also provide more room for inserts in an adenoviral vector, which may be of especial concern if an adenoviral vector will be packaged as a virus (see below). Even more importantly, deletion of endogenous TREs would prevent a possibility of a recombination event whereby an AFP-TRE is deleted and the endogenous TRE assumes transcriptional control of its respective adenovirus coding sequences (thus allowing non-specific replication). In one embodiment, an adenoviral vector of the invention is constructed such that the endogenous transcription control sequences of an adenoviral gene(s) are deleted and replaced by an AFP-TRE. However, endogenous TREs may also be maintained in the adenovirus vector(s), provided that sufficient cell-specific replication preference is preserved. These embodiments can be constructed by providing an AFP-TRE in addition to the endogenous TREs, preferably with the AFP-TRE intervening between the endogenous TREs and replication gene coding segment. Requisite cell-specific replication preference is indicated by conducting assays that compare replication of the adenovirus vector in a cell expressing AFP with replication in a non-AFP producing cell. Generally, a replication differential of at least about 2-fold is preferred; more preferably, at least about 5-fold; more preferably, at least about 10-fold; more preferably, at least about 50-fold; even more preferably, at least about 100-fold; still more preferably, at least about 200-fold; still more preferably, at least about 400-fold to about 500-fold; even more preferably, at least about 1000-fold. The acceptable differential can be determined empirically (using, for example, assays described in the Example section) and will depend upon the anticipated use of the adenoviral vector and/or the desired result.

Suitable target cells are any cell type that allows an AFP-TRE to function. Preferred are cells that express, or produce, or are capable of expressing or producing AFP, including, but not limited to, tumor cells expressing AFP. Examples of such cells are hepatocellular carcinoma cells, gonadal and other germ cell tumors (especially endodermal sinus tumors), brain tumor cells, ovarian tumor cells, acinar cell carcinoma of the pancreas (Kawamoto et al. (1992) *Hepatogastroenterology* 39:282–286), primary gall bladder tumor (Kat suragi et al. (1989) *Rinsko Hoshasen* 34:371–374), uterine endometrial adenocarcinoma cells (Koyama et al. (1996) *Jpn. J. Cancer Res.* 87:612–617), and any metastases of the foregoing (which can occur in lung, adrenal gland, bone marrow, and/or spleen). In some cases, metastatic disease to the liver from certain pancreatic and stomach cancers produce AFP. Especially preferred are hepatocellular carcinoma cells and any of their metastases. AFP production can be measured using assays standard in the art, such as RIA, ELISA or Western blots (immunoassays) to determine levels of AFP protein production or Northern blots to determine levels of AFP mRNA production. Alternatively, such cells can be identified and/or characterized by their ability to activate transcriptionally an AFP-TRE (i.e., allow an AFP-TRE to function).

Any of the various serotypes of adenovirus can be used, such as Ad2, Ad5, Ad12 and Ad40. For purposes of illustration, serotype Ad5 will be exemplified herein.

In some embodiments, an AFP-TRE is used with an adenovirus gene that is essential for propagation, so that replication competence is preferentially achievable in the target cell expressing AFP. Preferably, the gene is an early gene, such as E1A, E1B, E2, or E4. (E3 is not essential for viral replication.) More preferably, the early gene under AFP-TRE control is E1A and/or E1B and/or E4. More than one early gene can be placed under control of an AFP-TRE. Example 1 provides a more detailed description of such constructs.

The E1A gene is expressed immediately after viral infection (0–2 h) and before any other viral genes. E1A protein acts as a trans-acting positive-acting transcriptional regulatory factor, and is required for the expression of the other early viral genes E1B, E2, E3, E4, and the promoter-proximal major late genes. Despite the nomenclature, the promoter proximal genes driven by the major late promoter are expressed during early times after Ad5 infection. Flint (1982) *Biochem. Biophys. Acta* 651:175–208; Flint (1986) *Advances Virus Research* 31:169–228; Grand (1987) *Biochem. J.* 241:25–38. In the absence of a functional E1A gene, viral infection does not proceed, because the gene products necessary for viral DNA replication are not produced. Nevins (1989) *Adv. Virus Res.* 31:35–81. The transcription start site of Ad5 E1A is at 498 and the ATG start site of the E1A protein is at 560 in the virus genome.

The E1B protein functions in trans and is necessary for transport of late mRNA from the nucleus to the cytoplasm. Defects in E1B expression result in poor expression of late viral proteins and an inability to shut off host cell protein synthesis. The promoter of E1B has been implicated as the defining element of difference in the host range of Ad40 and Ad5: clinically Ad40 is an enterovirus, whereas Ad5 causes acute conjunctivitis. Bailey, Mackay et al. (1993) *Virology* 193:631; Bailey et al. (1994) *Virology* 202:695–706). The E1B promoter of Ad5 consists of a single high-affinity recognition site for Spl and a TATA box.

The E2 region of adenovirus codes for proteins related to replication of the adenoviral genome, including the 72 kDa DNA-binding protein, the 80 kD precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1a transactivator protein, the E2 early promoter is crucial during the early phases of viral replication.

The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site.

For a detailed review of the E2 promoter architecture see Swaminathan et al., *Curr. Topics in Micro. and Imm.* (1995) 199 part 3:177–194.

The E2 late promoter overlaps with the coding sequences of a gene encoded by the counterstrand and is therefore not amenable to genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor biding sites E2F and ATF. Therefore, insertion of an AFP-TRE having SpeI ends into the SpeI site in the l-strand would disrupt the endogenous E2 early promoter of Ad5 and should allow AFP-restricted expression of E2 transcripts.

The E4 gene has a number of transcription products. The E4 region codes for two polypeptides which are responsible for stimulating the replication of viral genomic DNA and for stimulating late gene expression. The protein products of open reading frames (ORFS) 3 and 6 can both perform these functions by binding the 55 kD protein from E1B and heterodimers of E2F-1 and DP-1. The ORF 6 protein requires interaction with the E1B 55 kD protein for activity while the ORF 3 protein does not. In the absence of functional protein from ORF 3 and ORF 6, plaques are produced with an efficiency less than $10^{-6}$ that of wild type virus. To further restrict viral replication to AFP-producing cells, E4 ORFs 1–3 can be deleted, making viral DNA replication and late gene synthesis dependent on E4 ORF 6 protein. By combining such a mutant with sequences in which the E1B region is regulated by an AFP-TRE, a virus can be obtained in which both the E1B function and E4 function are dependent on an AFP-TRE driving E1B.

The major late genes relevant to the subject invention are genes L1, L2, L3, L4, and L5 which encode proteins of the adenovirus virion. All of these genes (typically coding for structural proteins) are probably required for adenoviral replication. The late genes are all under the control of the major late promoter (MLP), which is located in Ad5 at +5986 to +6048.

In addition to conferring selective cytotoxic and/or cytolytic activity by virtue of preferential replication competence in cells that allow an AFP-TRE to function, such as cells expressing AFP, the adenovirus vectors of this invention can further include a heterologous gene (transgene) under the control of an AFP-TRE. In this way, various genetic capabilities may be introduced into target cells expressing AFP, particularly AFP-producing cancer cells. For example, in certain instances, it may be desirable to enhance the degree and/or rate of cytotoxic activity, due to, for example, the relatively refractory nature or particular aggressiveness of the AFP-producing target cell. This could be accomplished by coupling the cell-specific replicative cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin [Palmiter et al. (1987) *Cell* 50: 435; Maxwell et al. (1987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J. Biochem.* 148: 265; Frankel et al. (1989) *Mol. Cell. Biol.* 9: 415], genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly; genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-α, -β, -γ, TNF-α, -β, TGF-α, -β, NGF, and the like. The positive effector genes could be used in an earlier phase, followed by cytotoxic activity due to replication.

As discussed above, in some embodiments, the adenovirus death protein (ADP), encoded within the E3 region, is maintained (i.e., contained) in the adenovirus vector. The ADP gene, under control of the major late promoter (MLP), appears to code for a protein (ADP) that is important in expediting host cell lysis. Tollefson et al. (1996) *J. Virol.* 70(4):2296; Tollefson et al. (1992) *J. Virol.* 66(6):3633. Thus, adenoviral vectors containing the ADP gene may render the adenoviral vector more potent, making possible more effective treatment and/or a lower dosage requirement.

Accordingly, the invention provides adenoviral vectors that include a polynucleotide sequence encoding an ADP. A DNA sequence encoding an ADP and the amino acid sequence of an ADP are depicted in SEQ ID NO: 22 and SEQ ID NO: 23, respectively. Briefly, an ADP coding sequence is obtained preferably from Ad2 (since this is the strain in which ADP has been more fully characterized) using techniques known in the art, such as PCR. Preferably, the Y leader (which is an important sequence for correct expression of late genes) is also obtained and ligated to the ADP coding sequence. The ADP coding sequence (with or without the Y leader) can then be introduced into the adenoviral genome, for example, in the E3 region (where the ADP coding sequence will be driven by the MLP or the E3 promoter). The ADP coding sequence could also be inserted in other locations of the adenovirus genome, such as the E4 region. Alternatively, the ADP coding sequence could be operably linked to a heterologous promoter (with or without enhancer(s)), including, but not limited to, another viral promoter, a tissue specific promoter such as AFP, carcinoembryonic antigen (CEA), mucin, and rat probasin. Example 4 provides a description of an ADP construct in which the coding sequence for ADP was inserted into the E3 region of Ad5.

With respect to ADP, the cytotoxic properties, virus yield, and in vivo cytotoxic properties of an adenoviral vector that contains ADP encoding sequences were examined. The viral construct characterized, CN751, showed significant, efficient in vitro cell killing and viral yield when compared to a control vector not containing these sequences. Further, LNCaP (a prostate carcinoma cell line) tumor xenografts in nude mice either diminished in size or remained the same size (i.e., growth was suppressed) when compared to tumor size from those mice receiving control adenoviral vector or buffer, with a statistically significant difference in tumor size between CN751 and control treated tumors after seven days post-administration. Collectively, these data strongly suggest that an ADP-containing adenovector is an effective cytotoxic agent.

Accordingly, the invention also provides a non-naturally occurring adenoviral vector comprising a polynucleotide encoding an ADP polypeptide. It is understood that these vectors may contain multiple copies of ADP-encoding sequences, and that, if present in multiple copies, the sequences need not be the same, as long as an ADP polypeptide is produced from at least two these sequences. As discussed above, an "ADP polypeptide" is a polypeptide exhibiting at least one function associated with ADP, especially a function associated with cytotoxicity, preferably cell death. An "ADP polypeptide" includes forms of ADP discussed above, as well as any polypeptide fragment which exhibits ADP function. Because ADP function is associated with cytotoxic activity, particularly lysis, a putative ADP polypeptide can be tested by using methods standard in the art, such as plaque assays.

In some embodiments, the ADP polypeptide is a polypeptide sequence depicted in SEQ ID NO: 23, including the entire sequence of SEQ ID NO: 23. In other embodiments, the polynucleotide encoding the ADP polypeptide is depicted in SEQ ID NO: 22, including the entire sequence of SEQ ID NO: 22. Given an amino acid sequence of an ADP, it is possible using methods known in the art to design polynucleotides that encode for all or a portion of SEQ ID NO: 23 using polynucleotide sequences other than that depicted in SEQ ID NO: 22. Further, given tools such as degenerate probes that are readily made by those skilled in the art, it is possible to obtain and test other ADP sequences from, for example, other adenoviral serotypes.

The ADP-encoding sequence may or may not be under transcriptional control of a cell-specific, tissue-specific, and/or tumor-specific TRE. In some embodiments, the ADP polypeptide encoding sequence is under transcriptional control of a cell-specific TRE, such as, for example, an AFP-TRE or a prostate-cell specific TRE. Examples of a prostate-cell specific TRE is one derived from prostate specific antigen (U.S. Pat. Nos. 5,698,443 and 5,648,478), probasin (described in commonly owned patent application U.S. Ser. No. 60/039,762 and U.S. Ser. No. 09/033,333, and human kallikrien 2 (described in commonly owned patent application U.S. Ser. No. 60/076,545 and U.S. Ser. No. 60/054,523). Other examples of cell-specific TREs are carcinoembryonic antigen and mucin. Description of functional fragments for these and other TREs are available in the art.

In some embodiments, the invention provides adenoviral vectors which comprise an additional adenovirus gene under transcriptional control of a second AFP-TRE. Examples of an additional adenovirus gene under transcriptional control is ADP (discussed above) and genes necessary for replication, such as early genes. For example, an adenoviral vector can be constructed such that a first AFP-TRE regulates transcription of one early gene, such as E1A or E1B, and a second AFP-TRE regulates transcription of another early gene. These multiple constructs may be more desirable in that they provide more than one source of cell specificity with respect to replication (see Example 1). CN733, such a double construct, successfully inhibited tumor growth in nude mice harboring HuH7 tumor xenografts (Example 4).

Any of the adenoviral vectors described herein can be used in a variety of forms, including, but not limited to, naked polynucleotide (usually DNA) constructs; polynucleotide constructs complexed with agents to facilitate entry into cells, such as cationic liposomes or other cationic compounds such as polylysine; packaged into infectious adenovirus particles (which may render the adenoviral vector(s) more immunogenic); packaged into other particulate viral forms such as HSV or AAV; complexed with agents (such as PEG) to enhance or dampen an immune response; complexed with agents that facilitate in vivo transfection, such as DOTMA™, DOTAP™, and polyamines. Thus, the invention also provides an adenovirus capable of replicating preferentially in AFP-producing cells. "Replicating preferentially" means that the adenovirus replicates more in an AFP-producing cell than a non AFP-producing cell. Preferably, the adenovirus replicates at a significantly higher level in AFP-producing cells than non-AFP-producing cells; preferably, at least about 2-fold higher, preferably at least about 5-fold higher, more preferably at least about 10-fold higher, still more preferably at least about 50-fold higher, even more preferably at least about 100-fold higher, still more preferably at least about 400-fold to about 500-fold higher, still more preferably at least about 1000-fold higher, most preferably at least about $1 \times 10^6$ higher. Most preferably, the adenovirus replicates solely in AFP-producing cells (that is, does not replicate or replicates at very low levels in non AFP-producing cells).

If an adenoviral vector is packaged into an adenovirus, the adenovirus itself may also be selected to further enhance targeting. For example, adenovirus fibers mediate primary contact with cellular receptor(s) aiding in tropism. See, e.g., Amberg et al. (1997) Virol. 227:239–244. If a particular subgenus of an adenovirus serotype displayed tropism for a target cell type and/or reduced affinity for non-target cell types, such subgenus (or subgenera) could be used to further increase cell-specificity of cytoxicity and/or cytolysis.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are in vitro or in vivo).

If used as a packaged adenovirus, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 $\mu$g to about 1000 $\mu$g of an adenoviral vector can be administered. The adenoviral vector(s) may be administered one or more times, depending upon the intended use and the immune response potential of the host, and may also be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

The present invention also provides host cells comprising (i.e., transformed with) the adenoviral vectors described herein. Both prokaryotic and eukaryotic host cells can be used as long as sequences requisite for maintenance in that host, such as appropriate replication origin(s), are present. For convenience, selectable markers are also provided. Prokaryotic host cells include bacterial cells, for example, *E. coli, B. subtilis,* and mycobacteria. Among eukaryotic host cells are yeast, insect, avian, plant, *C. elegans* (nemotode) and mammalian. Examples of fungi (including yeast) host cells are *S. cerevisiae, Kluyveromyces lactis (K. lactis),* species of Candida including *C. albicans* and *C. glabrata, Aspergillus nidulans, Schizosaccharomyces pombe (S. pombe), Pichia pastoris,* and *Yarrowia lipolytica.* Examples of mammalian cells are COS cells, mouse L cells, LNCaP cells, Chinese hamster ovary (CHO) cells, human embryonic kidney (HEK) cells, and African green monkey cells. *Xenopus laevis* oocytes, or other cells of amphibian origin, may also be used. Host systems are known in the art and need not be described in detail herein. Suitable host cells also include any cells that produce AFP or any protein that is known to activate an AFP-TRE (whether this protein is produced naturally or recombinantly).

The present invention also includes compositions, including pharmaceutical compositions, containing the adenoviral vectors described herein. Such compositions are useful for administration in vivo, for example, when measuring the degree of transduction and/or effectiveness of cell killing in an individual. Preferably, these compositions further comprise a pharmaceutically acceptable excipient. These compositions, which can comprise an effective amount of an adenoviral vector of this invention in a pharmaceutically acceptable excipient, are suitable for systemic administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Remington's Pharmaceutical Sciences,* 18th Edition, Mack Publishing (1990) Pharmaceutical compositions also include lyophilized and/or reconstituted forms of the adenoviral vectors (including those packaged as a virus, such as adenovirus) of the invention.

The present invention also encompasses kits containing an adenoviral vector(s) of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow someone to detect the presence of AFP-producing cells in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.

Preparation of the Adenovirus Vectors of the Invention

The adenovirus vectors of this invention can be prepared using recombinant techniques that are standard in the art. Generally, an AFP-TRE is inserted 5' to the adenoviral gene of interest, preferably one or more early genes (although late gene(s) may be used). An AFP-TRE can be prepared using oligonucleotide synthesis (if the sequence is known) or recombinant methods (such as PCR and/or restriction enzymes). Convenient restriction sites, either in the natural adeno-DNA sequence or introduced by methods such as oligonucleotide directed mutagenesis and PCR, provide an insertion site for an AFP-TRE. Accordingly, convenient restriction sites for annealing (i.e., inserting) an AFP-TRE can be engineered onto the 5' and 3' ends of an AFP-TRE using standard recombinant methods, such as PCR.

Polynucleotides used for making adenoviral vectors of this invention may be obtained using standard methods in the art, such as chemical synthesis, by recombinant methods, and/or by obtaining the desired sequence(s) from biological sources.

Adenoviral vectors are conveniently prepared by employing two plasmids, one plasmid providing for the left hand region of adenovirus and the other plasmid providing for the right hand region, where the two plasmids share at least about 500 nt of middle region for homologous recombination. In this way, each plasmid, as desired, may be independently manipulated, followed by cotransfection in a competent host, providing complementing genes as appropriate, or the appropriate transcription factors for initiation of transcription from a CEA-TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acid Research* 11: 6003–6020; Bridge et al. (1989) *J. Virol.* 63: 631–638.

For convenience, plasmids are available that provide the necessary portions of adenovirus. Plasmid pXC.1 (McKinnon (1982) *Gene* 19:33–42) contains the wild-type left-hand end of Ad5. pBHG10 (Bett et al. (1994) *Proc. Natl. Acad. Sci USA* 91:8802–8806; Microbix Biosystems Inc., Toronto) provides the right-hand end of Ad5, with a deletion in E3. The deletion in E3 provides room in the virus to insert a 3 kb AFP-TRE without deleting the endogenous enhancer/promoter. Bett et al. (1994). The gene for E3 is located on the opposite strand from E4 (r-strand). pBHG11 provides an even larger E3 deletion (an additional 0.3 kb is deleted). Bett et al. (1994).

For manipulation of the early genes, the transcription start site of Ad5 E1A is at 498 and the ATG start site of the E1A protein is at 560 in the virus genome. This region can be used for insertion of an AFP-TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at 1339 of Ad5. By carrying out the PCR in two steps, where overlapping primers at the center of the region introduce a 30 sequence change resulting in a unique restriction site, one can provide for insertion of AFP-TRE at that site. Example 1 provides a more detailed description of an adenoviral vector in which E1A is under AFP-TRE control.

A similar strategy may also be used for insertion of an AFP-TRE to regulate E1B. The E1B promoter of Ad5 consists of a single high-affinity recognition site for Spl and a TATA box. This region extends from 1636 to 1701. By insertion of an AFP-TRE in this region, one can provide for cell-specific transcription of the E1B gene. By employing the left-hand region modified with an AFP-TRE regulating E1A as the template for introducing an AFP-TRE to regulate E1B, the resulting adenovirus vector will be dependent upon the cell-specific transcription factors for expression of both E1A and E1B. Example 1 provides a more detailed description of how such constructs can be prepared.

Similarly, an AFP-TRE can be inserted upstream of the E2 gene to make its expression cell-specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site. For a detailed review of the E2 promoter architecture see Swaminathan et al., *Curr. Topics in Micro. and Imm.* (1995) 199 (part 3):177–194.

The E2 late promoter overlaps with the coding sequences of a gene encoded by the counterstrand and is therefore not amenable to genetic manipulation. However, the E2 early promoter overlaps only for a few base pairs with sequences coding for a 33-kDa protein on the counterstrand. Notably, the SpeI restriction site (Ad5 position 27082) is part of the stop codon for the above mentioned 33 kDa protein and conveniently separates the major E2 early transcription initiation site and TATA-binding protein site from the upstream transcription factor binding sites E2F and ATF. Therefore, insertion of a PB-TRE having SpeI ends into the SpeI site in the 1-strand would disrupt the endogenous E2 early promoter of Ad5 and should allow AR-restricted expression of E2 transcripts.

For E4, one must use the right hand portion of the adenovirus genome. The E4 transcription start site is predominantly at 35609, the TATA box at 35638 and the first ATG/CTG of ORF 1 is at 35532. Virtanen et al. (1984) *J. Virol.* 51: 822–831. Using any of the above strategies for the other genes, an AFP-TRE may be introduced upstream from the transcription start site. For the construction of mutants in the E4 region, the co-transfection and homologous recombination are performed in W162 cells (Weinberg et al. (1983) *Proc. Natl. Acad. Sci.* 80:5383–5386) which provide E4 proteins in trans to complement defects in synthesis of these proteins. Alternatively, these constructs can be produced by in vitro ligation.

Preparation of ADP-containing adenoviral vectors follows principles outlined above and known in the art. If the ADP encoding sequence is to be introduced, it may be inserted recombinantly using methods such as those described in Examples 5 and 6. Alternatively, an adenoviral vector already containing an ADP encoding sequence may be used to construct a recombinant vector containing other added and/or manipulated elements, such as a TRE or transgene.

Methods of packaging adenovirus polynucleotides into adenovirus particles are known in the art and are described in the Examples.

Methods Using the Adenovirus Vectors of the Invention

The subject vectors can be used for a wide variety of purposes, which will vary with the desired or intended result. Accordingly, the present invention includes methods using the adenoviral vectors described above.

In one embodiment, methods are provided for conferring selective cytotoxicity in cells which allow an AFP-TRE to function (i.e., a target cell), preferably cells expressing AFP comprising contacting the cells with an adenovirus vector described herein. Cytotoxicity can be measured using standard assays in the art, such as dye exclusion, $^3$H-thymidine incorporation, and/or lysis.

In another embodiment, methods are provided for propagating an adenovirus specific for cells which allow an AFP-TRE to function, preferably mammalian cells expressing AFP. These methods entail combining an adenovirus vector with the cells, whereby said adenovirus is propagated.

Another embodiment provides methods of killing cells which allow an AFP-TRE to function, such as cells expressing AFP, in a mixture of cells, comprising combining the mixture of cells with an adenovirus vector of the present invention. The mixture of cells is generally a mixture of normal cells and cancerous cells producing androgen receptor, and can be an in vivo mixture or in vitro mixture.

The invention also includes methods for detecting cells which allow an AFP-TRE to function, such as cells expressing AFP, in a biological sample. These methods are particularly useful for monitoring the clinical and/or physiological condition of an individual (i.e., mammal), whether in an experimental or clinical setting. For these methods, cells of a biological sample are contacted with an adenovirus vector, and replication of the adenoviral vector is detected. Alternatively, the sample can be contacted with an adenovirus in which a reporter gene is under control of an AFP-TRE. Expression of the reporter gene indicates the presence of cells that allow an AFP-TRE to function, such as AFP-producing cells. Alternatively, an adenovirus can be constructed in which a gene conditionally required for cell survival is placed under control of an AFP-TRE. This gene may encode, for example, antibiotic resistance. The adenovirus is introduced into the biological sample, and later the sample is treated with an antibiotic. The presence of surviving cells expressing antibiotic resistance indicates the presence of cells which allow an AFP-TRE to function, such as cells producing (or capable of producing) AFP. A suitable biological sample is one in which AFP-producing cells may be or are suspected to be present. Generally, in mammals, a suitable clinical sample is one in which cancerous cells producing AFP, such as hepatocellular carcinoma cells, are suspected to be present. Such cells can be obtained, for example, by needle biopsy or other surgical procedure. Cells to be contacted may be treated to promote assay conditions, such as selective enrichment, and/or solubilization. In these methods, AFP-producing cells can be detected using in vitro assays that detect adenoviral proliferation, which are standard in the art. Examples of such standard assays include, but are not limited to, burst assays (which measure virus yield) and plaque assays (which measure infectious particles per cell). Propagation can also be detected by measuring specific adenoviral DNA-replication, which are also standard assays.

The invention also provides methods of modifying the genotype of a target cell, comprising contacting the target cell with an adenovirus vector described herein, wherein the adenoviral vector enters the cell.

The invention further provides methods of suppressing tumor cell growth, preferably a tumor cell that expresses AFP, comprising contacting a tumor cell with an adenoviral vector of the invention such that the adenoviral vector enters the tumor cell and exhibits selective cytotoxicity for the tumor cell. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage. "Suppressing" tumor growth indicates a growth state that is curtailed when compared to growth without contact with, i.e., transfection by, an adenoviral vector described herein.

The invention also provides methods of lowering the levels of a tumor cell marker in an individual, comprising administering to the individual an adenoviral vector of the present invention, wherein the adenoviral vector is selectively cytotoxic toward cells producing the tumor cell marker. Tumor cell markers include, but are not limited to, AFP, PSA, hK2, and carcinoembryonic antigen. Methods of measuring the levels of a tumor cell marker are known to those of ordinary skill in the art and include, but are not limited to, immunological assays, such as enzyme-linked immunosorbent assay (ELISA), using antibodies specific for the tumor cell marker. In general, a biological sample is obtained from the individual to be tested, and a suitable assay, such as an ELISA, is performed on the biological sample.

The invention also provides methods of treatment, in which an effective amount of an adenoviral vector(s) described herein is administered to an individual. Treatment using an adenoviral vector(s) is indicated in individuals with tumors such as hepatocellularcarcinoma. Also indicated are individuals who are considered to be at risk for developing AFP-associated diseases (including cancer), such as those who have had a family history of the disease(s), and/or have had disease that has been resected or treated in some other fashion, such as chemotherapy. Determination of suitability of administering adenoviral vector(s) of the invention will depend, inter alia, on assessable clinical parameters such as serological indications and histological examination of tissue biopsies. Generally, a pharmaceutical composition comprising an adenoviral vector(s) is administered. Pharmaceutical compositions are described above.

The amount of adenoviral vector(s) to be administered will depend on several factors, such as route of administration, the condition of the individual, the degree of aggressiveness of the disease, the particular PB-TRE employed, and the particular vector construct (i.e., which adenovirus gene(s) is under PB-TRE control).

If administered as a packaged adenovirus, from about $10^4$ to about $10^{14}$, preferably from about $10^4$ to about $10^{12}$, more preferably from about $10^4$ to about $10^{10}$. If administered as a polynucleotide construct (i.e., not packaged as a virus), about 0.01 μg to about 100 μg can be administered, preferably 0.1 μg to about 500 μg, more preferably about 0.5 μg to about 200 μg. More than one adenoviral vector can be administered, either simultaneously or sequentially. Administrations are typically given periodically, while monitoring any response. Administration can be given, for example, intratumorally, intravenously or intraperitoneally.

The adenoviral vectors of the invention can be used alone or in conjunction with other active agents, such as chemotherapeutics, that promote the desired objective.

The following examples are provided to illustrate but not limit the invention.

EXAMPLES

Example 1

Adenovirus Vectors Containing an AFP-TRE Driving Transcription of E1A and/or E1B A human embryonic kidney cell line, 293, efficiently expresses E1A and E1B genes of Ad5 and exhibits a high transfection efficiency with adenovirus DNA. For these experiments, 293 cells were co-transfected with one left end Ad5 plasmid and one right end Ad5 plasmid. Homologous recombination generates adenoviruses with the required genetic elements for replication in 293 cells which provide E1A and E1B proteins in trans to complement defects in synthesis of these proteins.

The plasmids to be combined were co-transfected into 293 cells using cationic liposomes such as Lipofectin (DOTMA:DOPE™, Life Technologies) by combining the two plasmids, then mixing the plasmid DNA solution (10 μg of each plasmid in 500 μl of minimum essential medium (MEM) without serum or other additives) with a four-fold molar excess of liposomes in 200 μl of the same buffer. The DNA-lipid complexes were then placed on the cells and incubated at 37° C., 5% $CO_2$ for 16 hours. After incubation the medium was changed to MEM with 10% fetal bovine serum and the cells are further incubated at 37° C., 5% $CO_2$, for 10 days with-two changes of medium. At the end of this time the cells and medium were transferred to tubes, freeze-thawed three times, and the lysate was used to infect 293 cells at the proper dilution to detect individual viruses as plaques.

Plaques obtained were plaque purified twice, and viruses were characterized for presence of desired sequences by PCR and occasionally by DNA sequencing. For further experimentation, the viruses were purified on a large scale by cesium chloride gradient centrifugation.

Using the above procedure, three replication competent, hepatocarcinoma cell-specific adenoviruses were produced: CN732, which contains an AFP-TRE driving the expression of the E1A gene; CN733, which contains two AFP-TREs driving expression of the E1A and E1B genes; and CN734, which contains an AFP-TRE driving E1B expression. The viruses were generated by homologous recombination in 293 cells and cloned twice by plaque purification. The structure of the genomic DNA was analyzed by PCR and sequencing of the junctions between the inserted sequences and the Ad genomic sequences to confirm that the viruses contained the desired structures. The structure of the viruses was also confirmed by Southern blot.

TABLE 1

Adenovirus vectors containing AFP-TRE

| Virus | Name | Left End Plasmid | Right End Plasmid |
|---|---|---|---|
| E1A-AFP | CN732 | CN219 | BHG10 |
| E1A/E1B-AFP | CN733 | CN224 | BHG10 |
| E1B-AFP | CN734 | CN234 | BHG10 |

Virus Construction

Plasmid pXC.1 was purchased from Microbix Biosystems Inc. (Toronto). pXC.1 contains Ad5 sequences from (nucleotide) 22 to 5790. We introduced an AgeI site 12 bp 5' to the E1A initiation codon (Ad5 547) by oligo-directed mutagenesis and linked PCR. To achieve this, pXC.1 was PCR amplified using primers:

5'-TCGTCTTCAAGAATTCTCA (15.133A) (SEQ ID NO: 3), containing an EcoRI site, and

5'-TTTCAGTCACCGGTGTCGGA (15.134B) (SEQ ID NO: 4), containing an extra A to introduce an AgeI site. This created a segment from the EcoRI site in the pBR322 backbone to Ad5 560. A second segment of pXC.1 from Ad 541 to the XbaI site at Ad nucleotide 1339 was amplified using primers:

5'-GCATTCTCTAGACACAGGTG (15.133B) (SEQ ID NO: 5) containing an XbaI site, and

5'-TCCGACACCGGTGACTGAAA (15.134A) (SEQ ID NO: 6), containing an extra T to introduce an AgeI site. A mixture of these two PCR amplified DNA segments was mixed and amplified with primers 15.133A and 15.133B to create a DNA segment from the EcoRI site to the XbaI site of pXC.1. This DNA segment encompasses the leftmost 1317 bases of Ad sequence and contains an AgeI site at Ad 547. This DNA segment was used to replace the corresponding segment of pXC. 1 to create CN95.

An EagI site was created upstream of the E1B start site by inserting a G residue at Ad5 1682 by oligonucleotide directed mutagenesis as above. To simplify insertion of an AFP-TRE in the EagI site the endogenous EagI site in CN95 was removed by digestion with EagI, treatment with mung bean nuclease, and re-ligation to construct CN114. The primers:

5'-TCGTCTTCAAGAATTCTCA (15.133A) (SEQ ID NO: 3), containing an EcoRI site, and

5'-GCCCACGGCCGCATTATATAC (9.4) (SEQ ID NO: 7), containing an EagI site, and

5'-GTATATAATGCGGCCGTGGGC (9.3) (SEQ ID NO: 8) containing an extra G and an EagI site, and 5'-CCAGAAAATCCAGCAGGTACC (24.020) (SEQ ID NO: 9), containing a KpnI site, were used to amplify the segment between 1682 and the KpnI site at Ad5 2048. Co-amplification of the two segments with primers 15.133A and 24.020 yielded a fragment with an EagI site at Ad5 1682 which was used to replace the corresponding EcoRI/KpnI site in pXC.1 to construct CN124.

For construction of CN732, human AFP enhancer domains A and B (included in the region −3954 bp to −3335 bp relative to the AFP cap site) were PCR amplified from human genomic DNA (Clontec, Palo Alto, Calif.) using the following primers:

5 'GTGACCGGTGCATTGCTGTGAACTCTGTA 3'
(39.055B) (SEQ ID NO: 10)
5'ATAAGTGGCCTGGATAAAGCTGAGTGG 3'
(39.044D) (SEQ ID NO: 11)

The AFP promoter was amplified from −163 to +34 using the following primers:

5' GTCACCGGTCTTTGTTATTGGCAGTGGT 3'
(39.055J) (SEQ ID NO: 12)
5' ATCCAGGCCACTTATGAGCTCTGTGTCCTT 3'
(29.055M) (SEQ ID NO: 13)

The enhancer and promoter segments were annealed, and a fusion construct was generated using overlap PCR with primers 39.055B and 39.055J. This minimal enhancer/promoter fragment was digested with PinA1 and ligated with CN124 using the engineered AgeI site 5' of the E1A cap site to produce CN219. The liver specific viral vector CN732 was generated by homologous recombination by cotransfecting 293 cells with CN219 and BHG10.

CN733 was constructed by using the following two PCR primers to amplify the enhancer/promoter element described above (−3954 to −3335 and −174 to +29):

5' TATCGGCCGGCATTGCTGTGAACTCT 3' (39.077A)
(SEQ ID NO: 14)
5' TTACGGCCGCTTTGTTATTGGCAGTG 3' (39.077C)
(SEQ ID NO: 15)

The PCR product was digested with EagI and ligated into similarly cut CN219. The resulting plasmid, CN224, contains two identical AFP regulatory elements, one each modulating expression of the E1A gene and the E1B gene. CN733 was generated by homologous recombination in 293 cells by cotransfecting CN224 and BHG10.

To make CN734, the AFP-TRE regulating the expression of the E1A gene was excised from CN224 by digesting the plasmid with PinA1 and religating the vector. The resulting plasmid, CN234, was co-transfected with BHG10 in 293 cells to generate CN734.

Virus Growth in Vitro

Growth selectivity of CN732, CN733, and CN734 was analyzed in plaque assays in which a single infectious particle produces a visible plaque by multiple rounds of infection and replication. Virus stocks were diluted to equal pfu/ml, then used to infect monolayers of cells for 1 hour. The inoculum was then removed and the cells were overlayed with semisolid agar containing medium and incubated at 37° C. for 10 days (12 days for Table 4). Plaques in the monolayer were then counted and titers of infectious virus on the various cells were calculated. The data were normalized to the titer of CN702 (wild type) on 293 cells. The results of four representative assays are shown in Tables 2–5.

TABLE 2

Plaque assay for 733 (E1A/E1B)

| Cell line | Virus | Titer | Avg. titre | Titre/293 | 702/733 |
|---|---|---|---|---|---|
| 293 (control) | 733 | $2.70 \times 10^6$ | $2.65 \times 10^6$ | 1 | N/A |
|  | 733 | $2.60 \times 10^6$ |  |  |  |
|  | 702 | $1.30 \times 10^6$ | $1.70 \times 10^6$ | 1 |  |
|  | 702 | $2.10 \times 10^6$ |  |  |  |
| Hep3B (AFP+) | 733 | $1.01 \times 10^7$ | $1.02 \times 10^7$ | 3.7 | .37 |
|  | 733 | $1.03 \times 10^7$ |  |  |  |

TABLE 2-continued

Plaque assay for 733 (E1A/E1B)

| Cell line | Virus | Titer | Avg. titre | Titre/293 | 702/733 |
|---|---|---|---|---|---|
|  | 702 | $1.00 \times 10^6$ | $7.02 \times 10^5$ | 1.36 |  |
|  | 702 | $5.00 \times 10^5$ |  |  |  |
| HepG2 (AFP+) | 733 | $9.70 \times 10^6$ | $1.04 \times 10^7$ | 3.92 | 0.292 |
|  | 733 | $1.10 \times 10^7$ |  |  |  |
|  | 702 | $1.60 \times 10^6$ | $1.95 \times 10^6$ | 1.14 |  |
|  | 702 | $2.30 \times 10^6$ |  |  |  |
| LNCaP (AFP−) | 733 | $4.00 \times 10^3$ | $3.00 \times 10^3$ | 0.0011 | 290 |
|  | 733 | $2.00 \times 10^3$ |  |  |  |
|  | 702 | $4.00 \times 10^5$ | $5.05 \times 10^5$ | 0.32 |  |
|  | 702 | $7.00 \times 10^5$ |  |  |  |
| HBL100 (AFP−) | 733 | 0 | 0 | 0 | 100–1000 |
|  | 733 | 0 |  |  |  |
|  | 702 | $1.00 \times 10^2$ | $3.07 \times 10^2$ | 0.00022 |  |
|  | 702 | $6.40 \times 10^2$ |  |  |  |

TABLE 3

CN732, CN733, CN734 Plaque Assay Data

| Cell line | Virus | Ave Titre | Titre/293 | 7XX/702 |
|---|---|---|---|---|
| 293 (control) | 702 | $1.2 \times 10^6$ | 1 |  |
|  | 732 | $6.15 \times 10^5$ | 1 |  |
|  | 733 | $2.20 \times 10^6$ | 1 |  |
|  | 734 | $2.50 \times 10^5$ | 1 |  |
| Huh-7 | 702 | $1.10 \times 10^4$ | 0.01375 |  |
|  | 732 | $1.10 \times 10^5$ | 0.1788 | 13 |
|  | 733 | $8.50 \times 10^4$ | 0.0386 | 3 |
|  | 734 | $1.90 \times 10^4$ | 0.076 | 6 |
| Sk-Hep-1 | 702 | $9.00 \times 10^2$ | 0.00113 |  |
|  | 732 | 0 | 0 | 0 |
|  | 733 | 0 | 0 | 0 |
|  | 734 | $1.00 \times 10^3$ | 0.004 | 4 |
| HeLa | 702 | $2.45 \times 10^2$ | 0.00030625 |  |
|  | 732 | 0 | 0 | 0 |
|  | 733 | 1.5 | $6.81 \times 10^{-7}$ | 0.0022 |
|  | 734 | $2.50 \times 10^1$ | 0.01 | 32 |
| MCF-7 | 702 | $3.10 \times 10^3$ | 0.003875 |  |
|  | 732 | 7.5 | $1.22 \times 10^{-5}$ | 0.0031 |
|  | 733 | $2.30 \times 10^1$ | $1.05 \times 10^{-5}$ | 0.0027 |
|  | 734 | $1.70 \times 10^3$ | 0.0068 | 2 |
| DLD-1 | 702 | $1.70 \times 10^3$ | 0.00213 |  |
|  | 732 | $1.40 \times 10^1$ | $2.28 \times 10^{-5}$ | 0.011 |
|  | 733 | 1 | $4.54 \times 10^{-7}$ | 0.00021 |
|  | 734 | $1.55 \times 10^3$ | 0.0062 | 3 |

TABLE 4

CN732, CN733, CN734 Plaquing Efficiency

| Cell line | Virus | Titre |
|---|---|---|
| 293 | 702 | $1 \times 10^7$ |
|  | 732 | $1 \times 10^7$ |
|  | 733 | $1 \times 10^7$ |
|  | 734 | $1 \times 10^7$ |
| HepG2 (AFP+) | 702 | $5 \times 10^6$ |
|  | 732 | $3 \times 10^6$ |
|  | 733 | $3 \times 10^6$ |
|  | 734 | $1 \times 10^7$ |
| Sk-Hep-1 (AFP−) | 702 | $6 \times 10^4$ |
|  | 732 | 0 |
|  | 733 | 0 |
|  | 734 | $3 \times 10^4$ |
| OVCAR-3 (AFP−) | 702 | $8 \times 10^5$ |
|  | 732 | 0 |
|  | 733 | 0 |
|  | 734 | $3 \times 10^4$ |

TABLE 4-continued

CN732, CN733, CN734 Plaquing Efficiency

| Cell line | Virus | Titre |
|---|---|---|
| HBL-100 | 702 | 2 × 10$^6$ |
| (AFP$^-$) | 732 | 0 |
|  | 733 | 0 |
|  | 734 | 1 × 10$^4$ |

TABLE 5

Plaque assay for CN732, CN733, and CN734

| Cell line | Virus | Ave Titre | Titre (cell line)/ Titer 293 | CN7XX/CN702 |
|---|---|---|---|---|
| 293 | 702 | 5.0 × 10$^6$ | 1 |  |
| (control) | 732 | 4.8 × 10$^6$ | 1 |  |
|  | 733 | 3.2 × 10$^6$ | 1 |  |
|  | 734 | 3.0 × 10$^8$ | 1 |  |
| HepG2 | 702 | 2.3 × 10$^7$ | 4.6 | — |
| (AFP$^+$) | 732 | 3.2 × 10$^7$ | 6.7 | 1.5 |
|  | 733 | 6.0 × 10$^6$ | 1.9 | 0.41 |
|  | 734 | 4.2 × 10$^8$ | 1.4 | 0.30 |
| DU145 | 702 | 2.2 × 10$^6$ | 0.44 | — |
| (AFP$^-$) | 732 | 3.0 × 10$^4$ | 0.0063 | 0.0143 |
|  | 733 | 3.1 × 10$^3$ | 0.00097 | 0.002 |
|  | 734 | 1.0 × 10$^7$ | 0.033 | 0.075 |
| HBL-100 | 702 | 4.0 × 10$^5$ | 0.8 | — |
| (AFP$^-$) | 732 | 0 | — | 0 |
|  | 733 | 0 | — | 0 |
|  | 734 | 6.0 × 10$^6$ | 0.02 | 0.025 |
| OVCAR-3 | 702 | 3.3 × 10$^5$ | 0.066 | — |
| (AFP$^-$) | 732 | 0 | — | 0 |
|  | 733 | 0 | — | 0 |
|  | 734 | 3.1 × 10$^5$ | 0.001 | 0.015 |

The wild type virus CN702 produced plaques on each of the cell lines tested. The number of plaques produced by CN702 was used as a base line against which to compare plaque formation by CN733.

In 293 cells growth of the viruses should be independent of the alterations to the E1 region due to the trans complimentation in this cell line. As expected, both CN702 and CN733 produced similar numbers of plaques on 293 cells.

Regarding the data from Table 1, in the AFP positive cell lines Hep3B and HepG2 CN702 produced similar numbers of plaques relative to 293 cells. In contrast CN733 produced approximately four fold more plaques in the AFP positive cell lines than in 293 cells. The super normal level of plaque formation by CN733 in the AFP positive lines indicates that the AFP enhancer is active in these cells.

In the AFP negative cell lines LNCaP and HBL100 growth of both viruses was curtailed but to different extents. Wild type CN702 virus produced plaques in LNCaP cells at approximately 30% of the level seen in 293 cells. In HBL-100 cells CN702 formed plaques at 0.02% of the level formed in 293 cells. CN733 plaque formation was diminished even further in these AFP negative cell lines relative to CN702. In LNCaP cells CN733 produced plaques at a level 0.1% of that seen in 293 cells. In HBL100 cells CN733 did not produce plaques at all. In comparison to CN702, the growth of CN733 on AFP negative cell lines was reduced by at least 100 fold. This compares favorably with previous results where the E1B promoter of Ad40 was shown to specify a differential of approximately 100 fold between gut and conjunctival epithelial tissues (Bailey et al., 1994) and with deletion mutants of the E1b gene which were shown to specify a 100 fold differential in Ad growth between p53+ and p53− cells (Bischoff et al., 1996). Lastly, comparison of the titer of an AFP+ cell type to the titer of an AFP− cell type provides a key indication that the, overall replication preference is enhanced due to depressed replication in AFP− cells as well as the replication in AFP+ cells.

Regarding the data from Table 3, several observations can be made. First, CN732, CN733, and CN734 all plaque as efficiently in Huh-7 cells as CN702. In contrast, the plaquing efficiency for two of the adenoviruses (CN732 and CN733) decreases dramatically in the non-AFP producing cell lines included in the experiment. In the non AFP producing hepatocellular carcinoma cell line Sk-Hep-1, CN732 and CN733 produced no plaques at the dilutions tested. The results are similar for these two viruses in Hela, MCF-7, and DLD-1. CN702's efficiency in DLD-1 cells exceeds CN733's by over 4000 fold.

With respect to the data in Table 4 (in which titers are normalized to 1×10$^7$ in 293 cells), CN732, CN733, and CN734 plaqued similarly to wild type (CN702) in HepG2 cells. However, these viruses plaqued poorly compared to CN702 in cell lines that do not express AFP. CN732 and CN733 produced no plaques at the dilutions tested in SK-Hep-1, OVCAR-3 and HBL-100, thus displaying significant titer differential. This corresponds to at least a 10,000 fold difference with wild type in HBL-100 and OVCAR-3 and a 1,000 fold difference in SK-Hep-1. CN734 also plaqued less efficiently than CN702 in OVCAR-3 (25 fold) and HBL-100 (200 fold) cells.

The data of Table 5 suggest that CN732, CN733, and CN734 plaque as efficiently as CN702 in cells that express AFP. However, they do not plaque as efficiently as CN702 in cell lines that do not express AFP. For example, neither CN732 nor CN733 produced any plaques at the dilutions tested in HBL100 cells or OVCAR-3 cells. CN734's plaquing differential was not as striking as CN732's or CN733's in the cell lines tested. It plaqued 13-fold, 40-fold, and 67-fold less efficiently than wild type in DU145, HBL100, and OVCAR-3, respectively.

The plaque assay data demonstrate that human adenovirus can be modified using an AFP-TRE to develop viruses with selective growth properties for AFP producing cells, particularly AFP-producing tumor cells such as hepatic carcinoma cells.

Western Analysis of EIA Expression

In the next experiment, we examined the effect of an AFP-TRE on the accumulation of E1A protein in CN733 infected cells. We reasoned that if one of the AFP regulatory regions installed in CN733 was modulating the E1A gene, the level of E1A protein in infected cells should also be affected. A western blot was conducted to test our hypothesis.

Figure 6A:
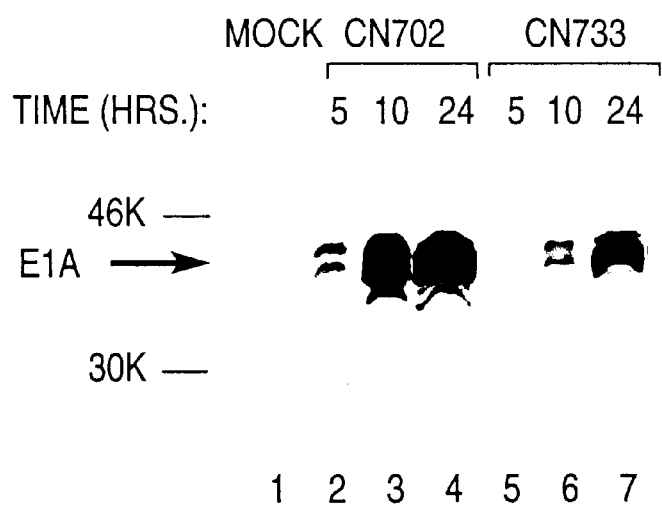
FIGS. 6(A), (B) and (C) are half tone reproductions depicting western analysis of E1A levels in CN733 (containing two AFP-TREs) and CN702 (control) infected cells.

CN733's E1A accumulation was evaluated in Huh-7, SK-Hep-1 and DLD-1 cells. Monolayers were infected with either CN702 or CN733 at an MOI of ten and the harvested at various time points after infection. Samples were electrophoresed through a 10% acrylimide gel and transferred by electrophoresis to a nitrocellulose membrane. E1A protein was detected by using the ECL Western Detection system (Amersham, Arlington Heights, Ill.) using the suggested protocol. The primary antibody used was rabbit anti-Ad2 E1A antibody (Santa Cruz Biotechnology, Santa Cruz, Calif.). The results are shown in FIG. 6(A).

E1A accumulated rapidly in CN702 and CN733 infected Huh-7 cells. A high level of E1A was also detected in CN702 infected Dld-1 cells. However, little E1A protein was detected in CN733 infected Dld-1 cells. This result is intriguing because it suggests that CN733's poor plaquing efficiency in non AFP producing cell lines could be attributed to its restricted E1A expression. These data are consistent with the hypothesis that the AFP-TRE affects CN733's compromised replication in non-permissive cell types.

Figure 6B:
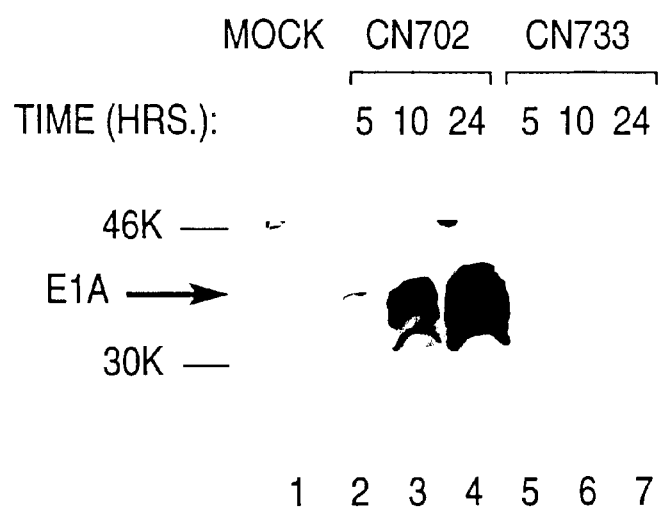
In FIG. 6(B), Sk-Hep-1 were the AFP−cells used.
Figure 6C:
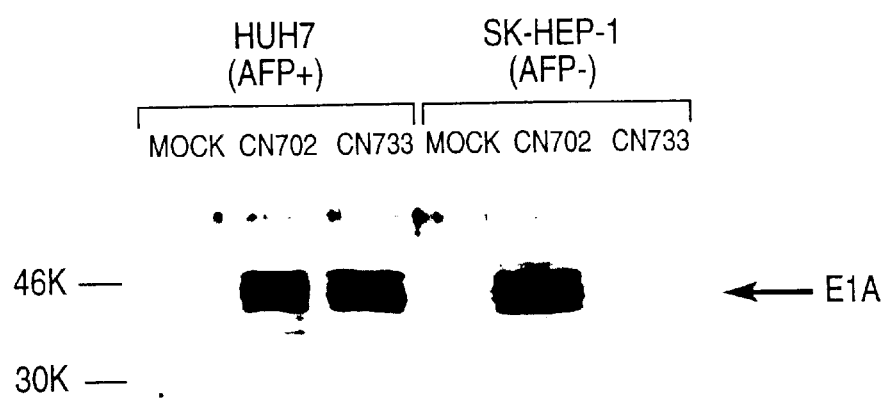

The experiment was repeated using Sk-Hep-1 cells as non AFP producing cells. Data were obtained after 24 hours post-infection. The results are shown in FIG. 6(B). The conclusion of this experiment is the same as the previous experiment: E1A expression is tightly regulated by the AFP-TRE.

Growth of CN733

Figure 7A:
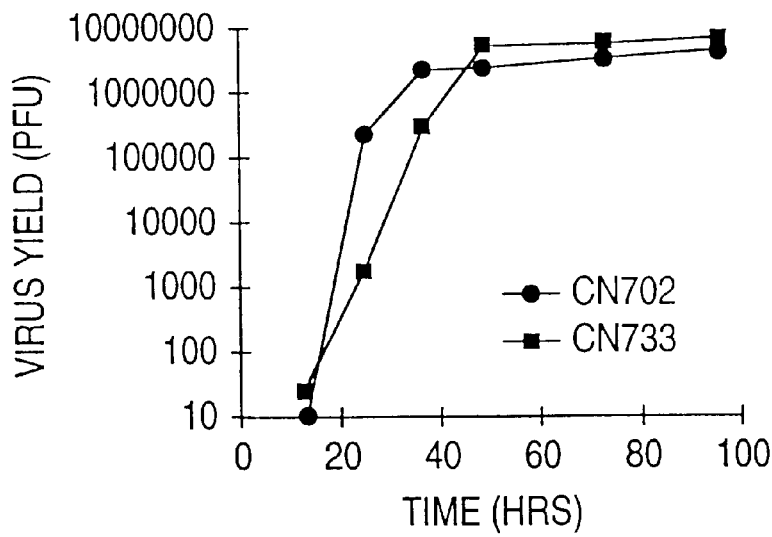
FIGS. 7(A)–(C) are graphs depicting growth of CN733 in AFP producing (Huh-7.
Figure 7B:
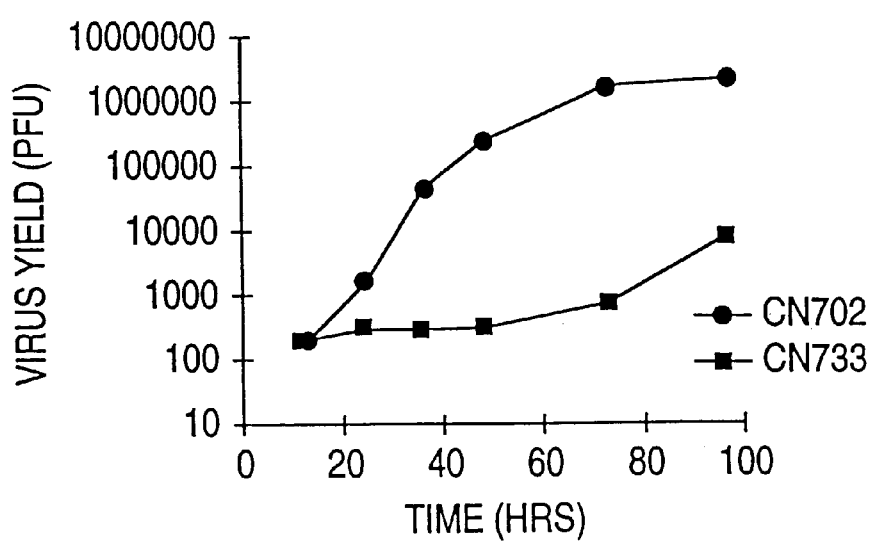
Figure 7C:
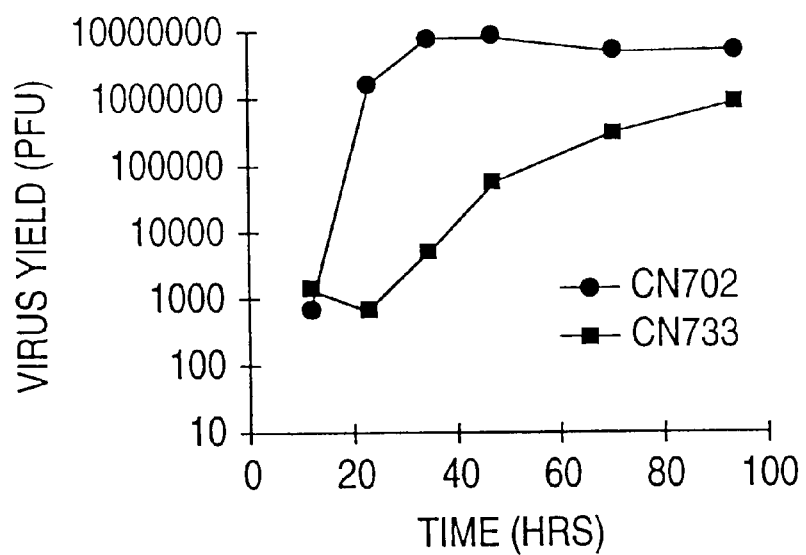

CN733's growth in AFP and non AFP producing cells was evaluated. Monolayers of Huh-7, Sk-Hep-1, and Dld-1 cells were infected at an MOI of ten with either CN702 or CN733. At various times after infection, duplicate samples were harvested, freeze-thawed three times, and titered on 293 cells to determine the total virus yield. Virus yield curves for CN702 and CN733 are plotted in FIGS. 7(A)–(C).

CN702 and CN733 grew efficiently in Huh-7 cells. Huh-7 cells produced similar amounts of infectious CN702 and CN733. In contrast, CN733's growth was severely restricted in SK-Hep-1 cells. CN702's titer at the conclusion of the experiment is about 1000 times greater than CN733's titer. The results were similar in Dld-1 cells.

Figure 8A:
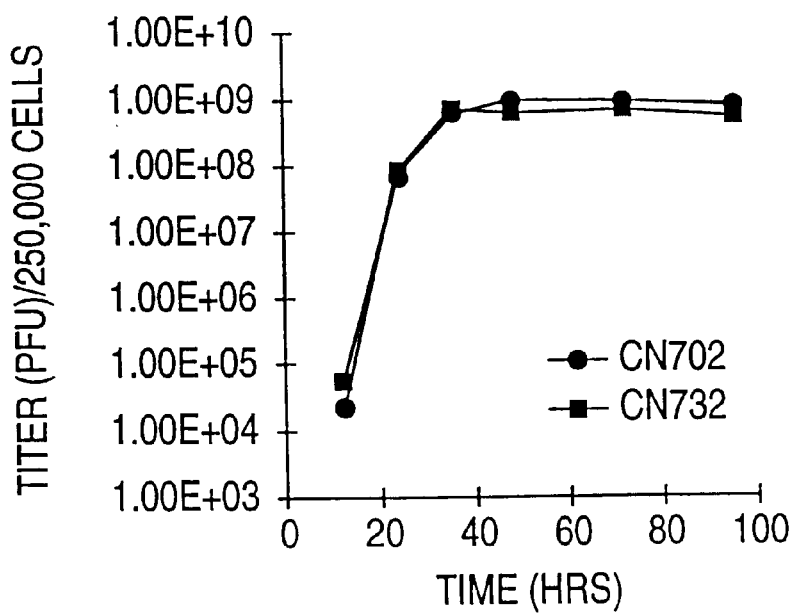
FIGS. 8(A)–(C) are graphs depicting growth of CN732 (FIG. 8(A); solid diamonds), CN733 (FIG. 8(B); solid diamonds), and CN734 (FIG. 8(C); solid diamonds) in HepG2 cells, as compared to control CN702 (solid squares).
Figure 8B:
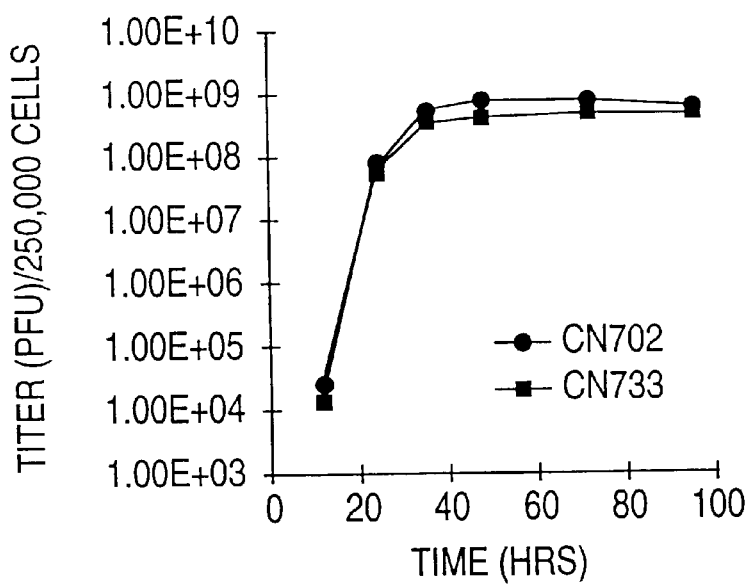
Figure 8C:
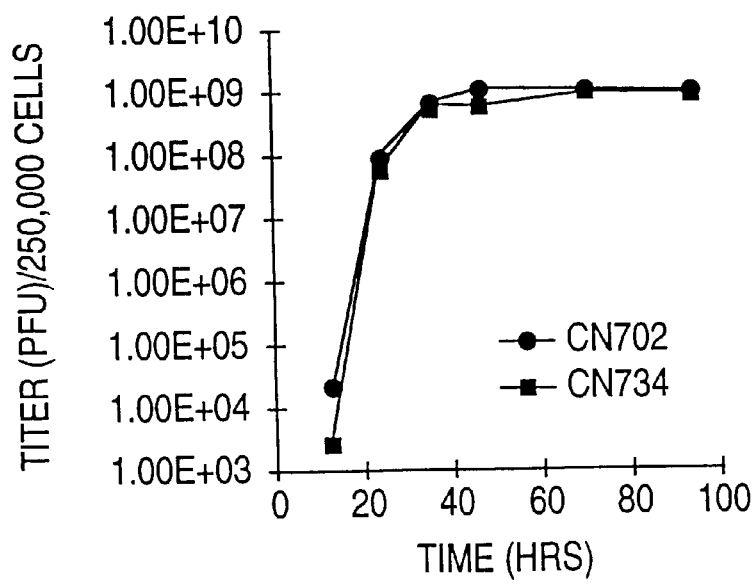

The growth experiment was also performed to compare growth of CN732, CN733, and CN734 in HepG2 cells. Monolayers of HepG2 cells were infected at a multiplicity of infection (MOI) of two and harvested at various times after infection. Samples were titered on 293 cells to determine the final virus yield. The results are shown in in FIGS. 8(A)–(C). The data demonstrate that the adenovirus containing AFP-TREs grow efficiently in this cancer cell line. CN732, CN733, and CN734 each reach a high final titer at 36 hours post infection that is similar to that of CN702.

Figure 9A:
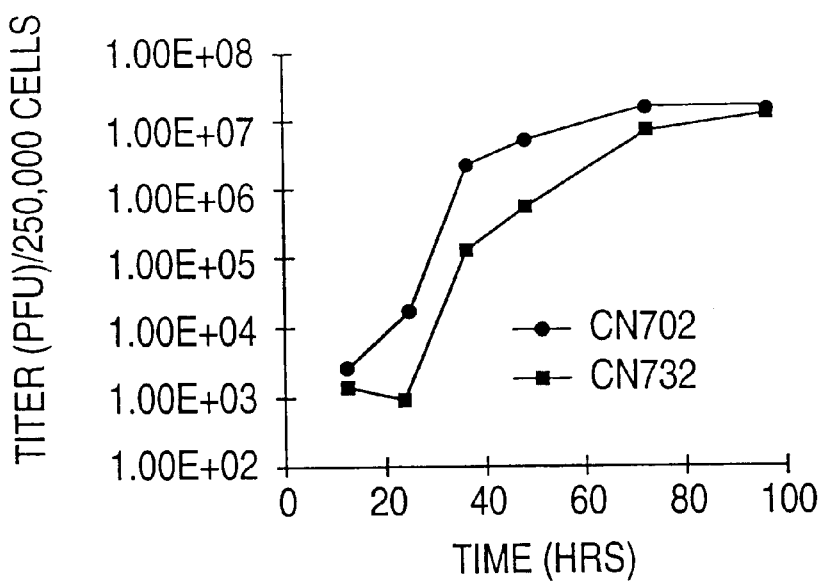
FIGS. 9(A)–(C) are graphs depicting growth of CN732 (FIG. 9(A); solid squares), CN733 (FIG. 9(B); solid circles), and CN734 (FIG. 9(C); solid circles) in primary hepatocytes, compared to control CN702 (solid diamonds).
Figure 9B:
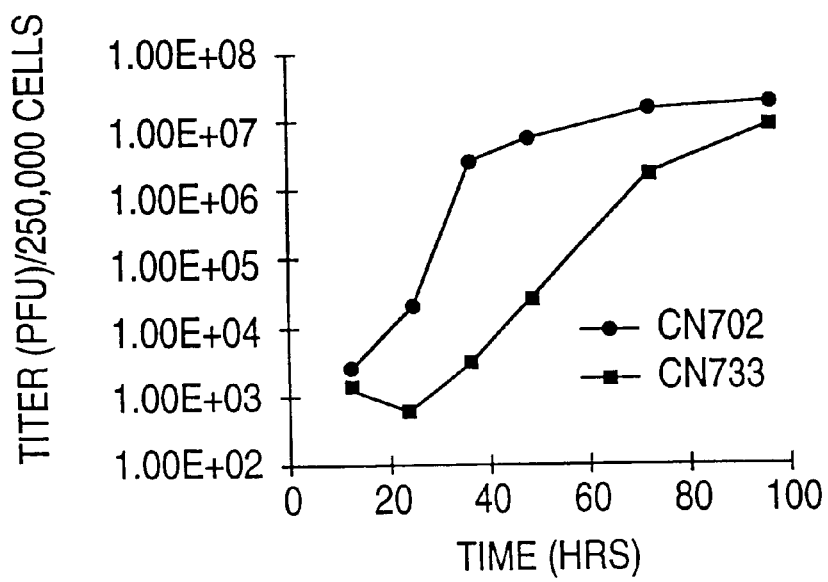
Figure 9C:
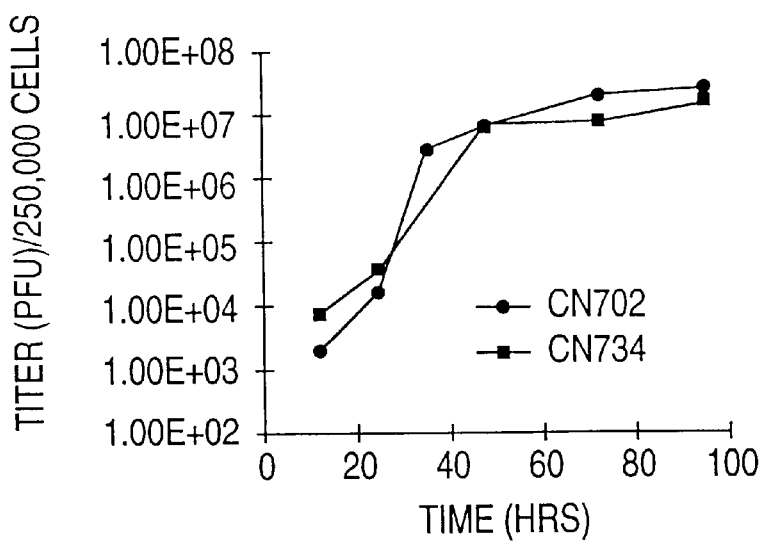

In another experiment, propagation was evaluated in primary hepatocytes (hNheps) isolated from a donor (32 year old black male) three days before the start of the experiment. Monolayers of cells were infected with virus at an MOI of two, harvested at various times after infection and titered on 293 monolayers. The results are shown in FIGS. 9(A)–(C). The data suggest that CN732 and CN733 grow less efficiently in hNheps than CN702. CN732's growth is delayed by twenty-four hours compared to CN702's. At thirty-six hours post infection, there is over ten fold more infectious CN702 than CN733. CN733's growth is delayed by thirty-six hours. At thirty-six hours post infection, there is nearly 1000 times more infections CN702 than CN733. CN734 grows similarly to CN702. The data also suggest that CN733 has the most restrictive phenotype, followed by CN732 and CN734. Taken together, these results also indicate that an AFP-TRE inserted upstream of the E1A gene may be more effective in restricting host-range than an AFP-TRE engineered upstream of the E1B region. The presence of two AFP-TREs is even more effective.

In conclusion, the experiments described above indicate that it is possible to restrict an adenoviral vector's host range to AFP producing cells. As demonstrated by plaque assay and growth assay, the adenovirus vectors containing an AFP-TRE propagate efficiently in HepG2 and Huh-7 cells but poorly in non AFP producing cells.

Example 2

Transient Expression Assay with Plasmid CN236

The ability of the 800 bp AFP-TRE in CN236 to drive expression of luciferase gene was determined in a transient expression assay. Chang liver cells, which do not make AFP and Hep3B cells, which produce AFP, were transformed with CN236 or pGL2Luc using the cationic lipids (i.e., lipofectin) method. pGL2-Basic (Promega) is a construct that does not contain the AFP regulatory gene only the backbone the gene was inserted into, hence it is the negative control construct for the assay. The plasmid vector, pGL2-Luc (Promega) served as a positive control. Cells were cultured in DMEM supplemented with 10% fetal calf serum (FCS) and, 48 hours later, assayed for luciferase activity. Luciferase activity was measured according to manufacturer's instructions in the kit (Packard Instruments) and quantitated using a luminometer. The results, shown in Table 6, below, are expressed in relative light units (RLUs).

TABLE 6

| Cell Line | Negative Control | pGL2-Luc | CN236 |
| --- | --- | --- | --- |
| Hep3B | 0.017 | 4.118 | 7549 |
| Chang Liver | 0.29 | 2.94 | 7.0 |

These data indicate that the fragment of DNA is active in AFP positive liver cells (Hep3B), but not AFP negative liver cells (Chang liver).

Example 3

Testing Cytotoxic Ability of Adenovirus Vectors on HuH7 Tumor Xenografts

An especially useful objective in the development of AFP-specific adenoviral vectors is to treat patients with AFP-producing tumors, such as hepatocellular carcinoma. An initial indicator of the feasibility is to test the vector(s) for cytotoxic activity against HuH7 tumor xenografts grown subcutaneously in Balb/c nu/nu mice. Mice are given s.c. injections with $1\times10^7$ HuH7 carcinoma cells in PBS. Tumor cells can be tested for AFP production by assaying for AFP in serum using standard assays (for example, ELISA).

For this experiment, test adenovirus vectors are introduced into the mice either by direct intratumoral, intravenous, or intraperitoneal injection of approximately $10^8$ pfu of virus (if administered as a packaged virus) in 0.1 ml PBS+10% glycerol or intravenously via the tail vein. If administered as a polynucleotide construct (i.e., not packaged into virus), 0.1 $\mu$g to 100 $\mu$g or more can be administered. Tumor sizes are measured and, in some experiments, blood samples are taken weekly. The effect of intratumoral injection of the adenoviral vector (such as CN733) on tumor size and serum AFP levels is compared to sham treatment.

While it is highly possible that a therapeutic based on the viruses described here would be given intralesionally (i.e., direct injection), it would also be desirable to determine if intravenous (IV) administration of adenovirus vector can affect tumor growth. If so, then it is conceivable that the virus could be used to treat metastatic tumor deposits inaccessible to direct injection. For this experiment, groups of three to five mice bearing HuH7 tumors are inoculated with $10^8$ pfu of an adenoviral vector (such as CN733) by tail vein injection, or with buffer used to carry the virus as a negative control. The effect of IV injection of the adenoviral vector on tumor size and serum AFP levels is compared to sham treatment.

Example 4

Testing Cytotoxic Ability of Adenovirus Vector CN733 on HepG2 Tumor Xenographs

Figure 10A:
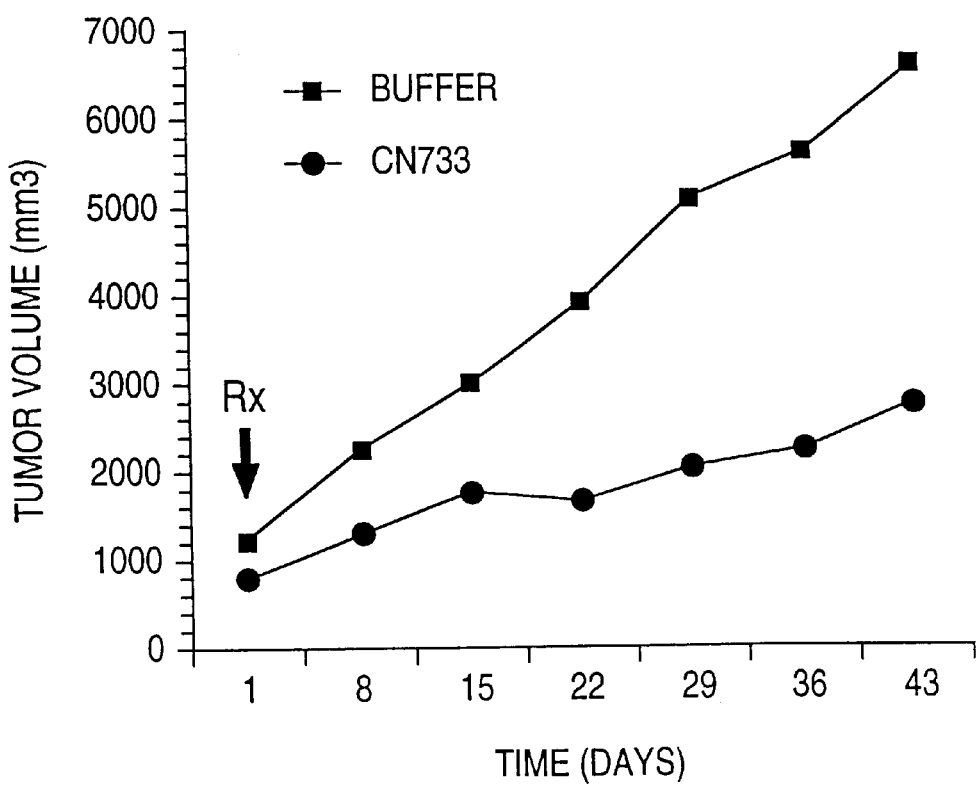
FIGS. 10(A)–(B) are graphs comparing tumor volume in mice harboring hepatocarcinoma cell line HepG2 and treated with CN733 (FIG. 9(A); squares) or with control buffer (circles).

An HCC mouse xenograft model was used to evaluate CN733's potential as a therapeutic adenovirus for liver cancer. The AFP producing HCC cell line HepG2 was injected subcutaneously on the right flanks of Balb/c nu/nu mice. After allowing several weeks for the tumors to take, each was treated with an intratumoral injection of either $1.5\times10^{11}$ particles of CN733 in PBS, glycerol or buffer alone. Eleven mice bearing HepG2 tumors were treated, six with CN733 and five with buffer. Tumors were measured weekly until the conclusion of the experiment. Tumor volume was calculated by multiplying the tumor's length by the square of its width and dividing the product by two. FIG. 10(A) is a graph of average tumor volume for each treatment group vs. time.

In six weeks, HepG2 tumors challenged with buffer grew to over five times their original size. In contrast, tumor growth in CN733 treated mice was attenuated. One tumor even regressed to 3% of its maximum volume. These data suggest that CN733 invaded the tumors and delivered cytotoxicity.

Figure 11:
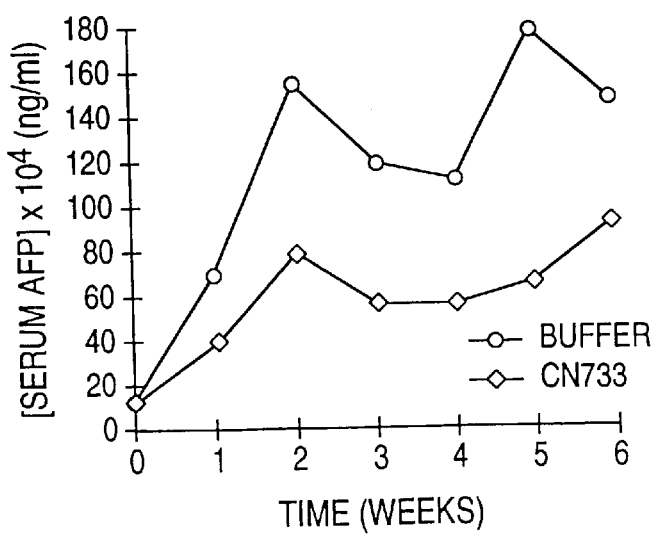
FIG. 11 is a graph depicting serum AFP levels in tumor-bearing mice receiving CN733 (triangles) or receiving buffer (circles).

In addition to monitoring tumor growth, we harvested serum samples and assayed AFP levels. The results are shown in FIG. 11. The data suggest that serum AFP levels rises more slowly in mice receiving CN733 than in control mice receiving buffer.

Figure 10B:
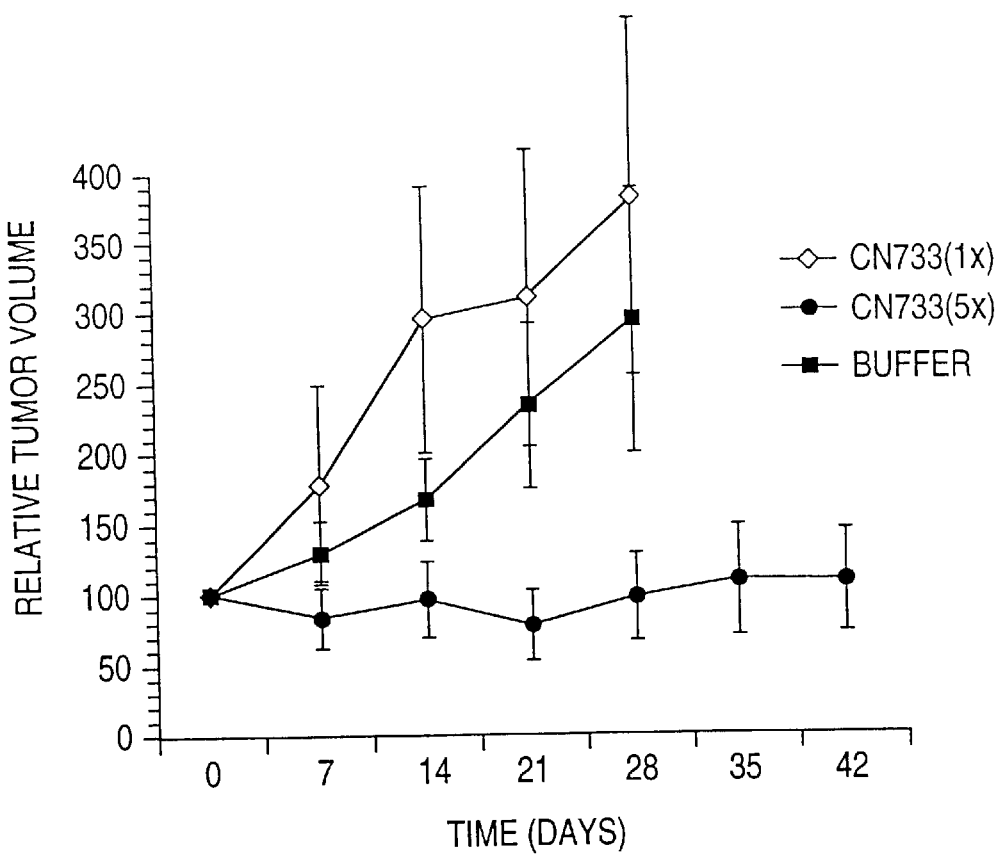

In another experiment, antitumor activity of different administrative regimens was compared for CN733. Animals were treated with a single intramuoral administration of either buffer (n=8, volume=919 mm³) or $1.5\times10^{11}$ particles of CN733 (n=8, volume 944 mm³). A third group of animals was treated with five consecutive daily doses of $1.5\times10^{11}$ particles of CN733 (n=8, volume=867 mm³). Despite the large systemic virus burden, the mice displayed no obvious signs of toxicity. Tumors were measured weekly by external caliper for four weeks after injection. Animals from groups treated with a single dose of CN733 and buffer were sacrificed four weeks after treatment because of excessive tumor burden. All animals from the group treated with five doses of CN733 survived until the conclusion of the study. Despite the large systemic virus burden, these animals showed no obvious signs of treatment related toxicity. The results are shown in FIG. 10(B). On average, buffer treated tumors increased to three times their initial volume by four weeks after treatment. Tumors treated with a single dose of CN733 increased to nearly four times their initial volume. In contrast, tumors treated with five doses of CN733 remained the same volume. Five out of eight tumors (63%) responded to treatment. One animal had no palpable tumor at the end of the study.

Statistical analysis using the Students T-test suggests that there was no significant difference at any time point between buffer treated animals and those treated with one dose of CN733 (p>0.5). However, there was a significant difference between buffer treated animals and those treated with five doses of CN733 beginning at two weeks post injection (p=0.045) and continuing through four weeks (p=0.034).

The data suggest that CN733 exhibits significant antitumor activity in HepG2 nude mouse xenografts. CN733 administered daily for five consecutive days at a dose of $1.5\times10^{11}$ particles can cause tumor regression in some animals. A single dose, however, is not sufficient to cause tumor killing.

In the first experiment, the tumors responded to a single dose of CN733 but did not appear to respond in the second. The inventors note that there is often a variation in tumor phenotype (including growth characteristics and AFP expression) from experiment to experiment.

In conclusion, the in vivo experiments suggest that CN733 causes significant tumor killing in large hepatoma xenografts. Five doses of intratumorally adminstered virus induced regression in four out of eight animals and cured one animal twenty-eight days after injection. On average, buffer treated tumors tripled while CN733 treated tumors remained the same.

Example 5

Construction of an Adenoviral Vector Containing the Coding Region for the Adenovirus Death Protein (ADP)

In AFP-specific viral vector CN733 (described above in Example 1), a deletion had been created in the E3 region to accomodate the AFP-TRE in the E1 region. The ADP coding sequence from Ad2 was reintroduced into the E3 region of Ad5 as follows.

An ADP cassette was constructed using overlap PCR. The Y leader, an important sequence for correct expression of some late genes, was PCR amplified using primers:

5' GCCTTAATTAAAAGCAAACCTCACCTCCG . . . Ad2 28287bp (37.124.1) (SEQ ID NO: 16); and 5' GTGGAACAAAAGGTGATTAAAAAATCCCAG . . . Ad2 28622bp (37.146.1) (SEQ ID NO: 17).

The ADP coding region was PCR amplified using primers

5' CACCTTTTGTTCCACCGCTCTGCTTATTAC . . . Ad2 29195bp (37.124.3) (SEQ ID NO: 18) and 5' GGCTTAATTAACTGTGAAAGGTGGGAGC . . . Ad2 29872bp (37.124.4) (SEQ ID NO: 19).

The two fragments were annealed and the overlap product was PCR amplified using primers 37.124.1 and 37.124.4. The ends of the product were polished with Klenow fragment and ligated to BamHI cut pGEM-72(+) (CN241; Promega, Madison, Wis.). The ADP cassette was excised by digesting CN241 with Pac 1 restriction endonuclease and ligated with two vectors, CN247 andCN248 generating plasmids CN252 and CN270, respectively. CN247 contains a unique PacI site in the E3 region and was constructed as follows. A plasmid containing the full length Ad5 genome, TG3602 (Transgene, France), was digested with BamHI and religated to yield CN221. The backbone of this plasmid (outside of the Ad5 sequence) contained a PacI site that needed to be removed to enable further manipulations. This was effected by digesting CN221 with PacI and polishing the ends with T4 DNA polymerase, resulting in CN246. CN246 was digested with AscI and AvrII (to remove intact E3 region). This fragment was replaced by a similarly cut fragment derived from BHG11. The resulting plasmid, CN 247, contained a deleted E3 region and a PacI site suitable for insertion of the ADP cassette fragment (described above). Ligation of CN247 with the ADP cassette generated CN252.

CN248 (a construct that would allow introduction of an ADP cassette into Ad that also contains a deletion/substitution in the E4 region) was made as follows. The E4 region was deleted by digesting CN108, a construct that contains right hand end Ad5 sequence from the unique EcoRI site in the E3 region (derived from BHG10), with AvrII and AflIII. The only E4 ORF necessary for viral replication, ORF 6, was reintroduced by PCR amplifying the ORF with primers, 33.81.1 (Ad5 33096):
GCAGCTCACTTAAGTTCATGTCG (SEQ ID NO: 20)

33.81.2 (Ad5 34084):
TCAGCCTAGGAAATATGACTACGTCCG (SEQ ID NO: 21)

The resulting plasmid is CN203. CN203 was digested with EcoRI and ligated to CN209, a shuttle plasmid, to generate CN208. In the final cloning step, CN208 was digested with AscI and AvrII and ligated to similarly cut E4 deletion/substitution with the ADP cassette.

Both CN252 and CN270 contain an E3 deletion. In addition, CN270 lacks some sequence in the E4 region as previously described. Adenoviral vectors are obtained via in vitro ligation of (1) appropriately prepared viral DNA digested with BamHI and (2) CN252 or CN257 also digested with BamHI. The ligation product is used to transfect 293 cells. Plaque assays are performed as described in Example 1.

Example 6

Characterization of an E3 Deleted Adenovirus, CN751, that Contains the Adenovirus Death Protein Gene An adenovirus death protein mutant, CN751, was constructed to test whether such a construct may be more effective for cytotoxicity. The adenovirus death protein (ADP), an 11.6 kD Asn-glycosylated integral membrane peptide expressed at high levels late in infection, migrates to the nuclear membrane of infected cells and affects efficient lysis of the host. The Adenovirus 5 (Ad5) E3 region expresses the adp gene.

Construction of CN751

CN751 was constructed in two parts. First, an E3 deleted platform plasmid that contains Ad5 sequence 3' from the BamHI site at 21562bp was generated. The Ad2 adp was engineered into the remainder of the E3 region of this plasmid to yield CN252 (this cloning has been previously described). To construct the second part, the 5' Ad5 sequence necessary for CN751 was obtained by digesting purified CN702 DNA with EcoRI and isolating the left hand fragment by gel extraction. After digesting CN252 with EcoRI, the left hand fragment of CN702 and CN252 were ligated. 293 cells were transfected with this ligation mixture by lipofection transfection and incubated at 37° C. Ten days later, the cells were harvested, freeze-thawed three times, and the supernatant was plaqued on 293 monolayers. Individual plaques were picked and used to infect monolayers of 293 cells to grow enough virus to test. After several days, plate lysates were screened using a polymerase chain reaction (PCR) based assay to detect candidate viruses. One of the plaques that scored positive was designated CN751.

Structural Characterization of CN751

The structure of CN751 was confirmed by two methods. First, primers 37.124.1 (5' GCCTTAATTAAAAGCAAAC-CTCACCTCCG Ad2 28287bp; SEQ ID NO: 16) and 37.124.4 (5' GGCTTAATTAACTGTGAAAG-GTGGGCTGC Ad2 29872bp; SEQ ID NO: 19) were used to screen candidate viruses by PCR to detect the presence of the adp cassette. CN751 produced an extension fragment consistent with the expected product (1065bp). Second, CN751 was analyzed by Southern blot. Viral DNA was purified, digested with PacI, SacI, and AccI/XhoI, and probed with a sequence homologous to the ADP coding region. The structure of CN751 matched the expected pattern.

In Vitro Characterization of CN751

Two experiments were conducted to examine the cytotoxicity and virus yield of CN751. In the first study, CN751's cytotoxicity was evaluated in LNCaP cells by measuring the accumulation of a cytosolic enzyme, lactate dehydrogenase (LDH), in the supernatant over several days. The level of extracellular LDH correlates with the extent of cell lysis. Healthy cells release very little, if any, enzyme, whereas dead cells release large quantities. LDH was chosen as a marker because it is a stable protein that can be readily detected by a simple protocol. CN751's ability to cause cell death was compared to that of CN702, a vector lacking the ADP gene, and Rec700, a vector containing the ADP gene.

Monolayers of LNCaP cells were infected at an MOI of one with either CN702, Rec700 (adp+ control), or CN751 and then seeded in 96 well dishes. Samples were harvested once a day from one day after infection to five days after infection and scored using Promega's Cytotox 96 kit. This assay uses a coupled enzymatic reaction which converts a tetrazolium salt to a red formazan product that can be determined in a plate reader at 490 nm.

Figure 12:
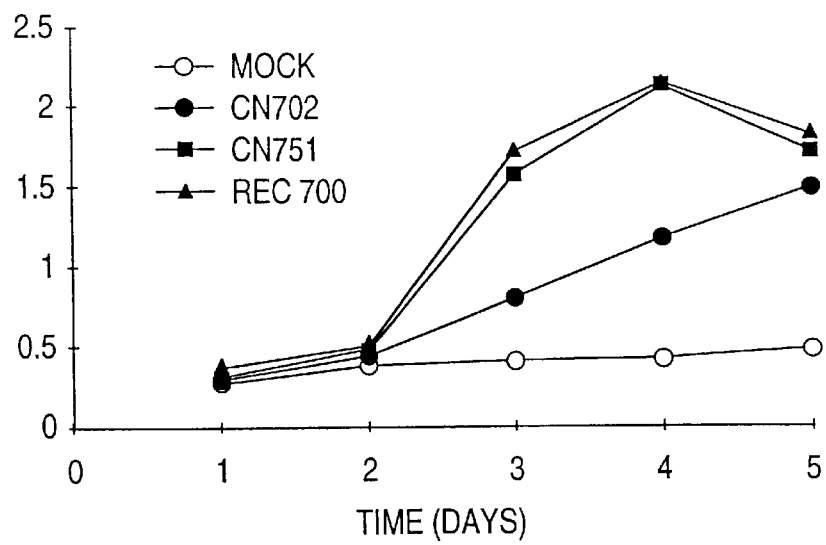
FIG. 12 is a graph depicting cytotoxicity of an adenoviral vector containing the coding sequence for adenoviral death protein (ADP), CN751 (solid squares), compared to control CN702 (solid circles), Rec 700 (solid triangles) and mock infection (Xs).

Since the absorbance of a sample corresponds to the level of LDH released from infected cells, a plot of how a sample's absorbance changes with time describes how efficiently the viruses studied induce cell lysis (FIG. 12). Each data point represents the average of sixteen separate samples. The results suggest that CN751 kills cells more efficiently than the adp– control, CN702, and similarly to the adp+ control, Rec700. The concentration of LDH in the supernatant increases rapidly from two days and reaches a maximum at four days in wells infected with CN751. In contrast, LDH concentration in the supernatant of CN702 infected cells begins to rise slowly at two days and continues until the conclusion of the experiment. Significantly, the amount of LDH released from CN751 infected cells at three days is two times that released from CN702 infected cells. The data demonstrate that adenovectors with the ADP gene kill cells more efficiently than adenovectors that lack the ADP gene.

Figure 13:
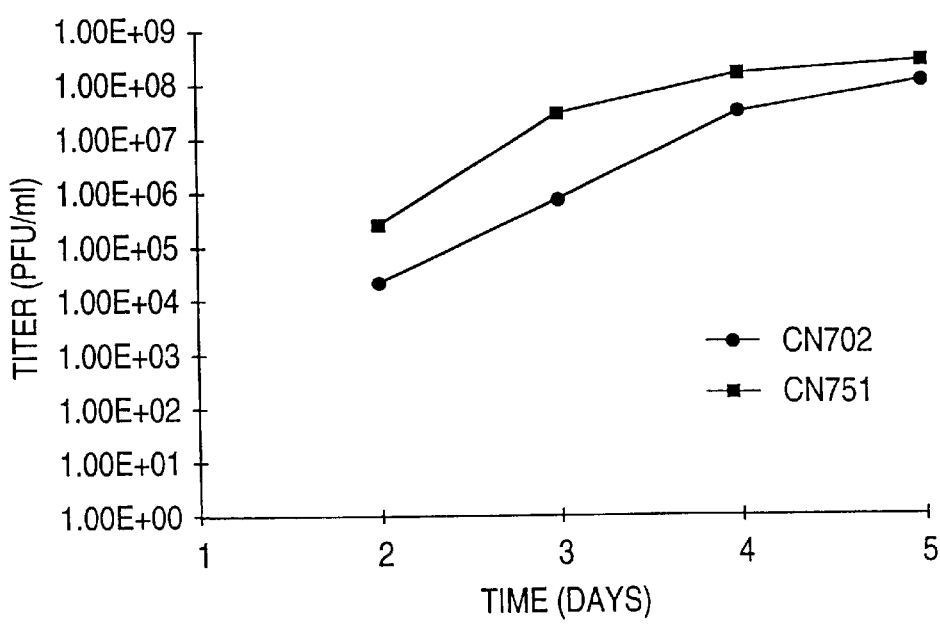
FIG. 13 is a graph comparing extracellular virus yield of CN751 (solid squares) and CN702 (solid circles).

Not only is it important for Ad vectors to kill cells efficiently, they must also be able to shed progeny that can infect other cancer cells. Viral vectors that can shed large amounts of virus might be better therapeutics than those that shed only small amounts. A virus yield assay was undertaken to evaluate whether CN751 can induce the efficient release of its progeny from the infected cell. A549 cells were infected at an MOI of five. Supernatant was harvested at various times after infection and titered on 293 cells to determine the virus yield (FIG. 13). The data suggest that cells infected with CN751 shed virus more efficiently than those infected with CN702. At forty-eight hours post infection, CN751 infected cells released ten times more virus than CN702 infected. At seventy-two hours post infection, CN751 infected cells released forty times more virus. In sum, the virus yield data demonstrate that adenovectors with the ADP gene release more virus.

In Vivo Characterization of CN751

Figure 14:
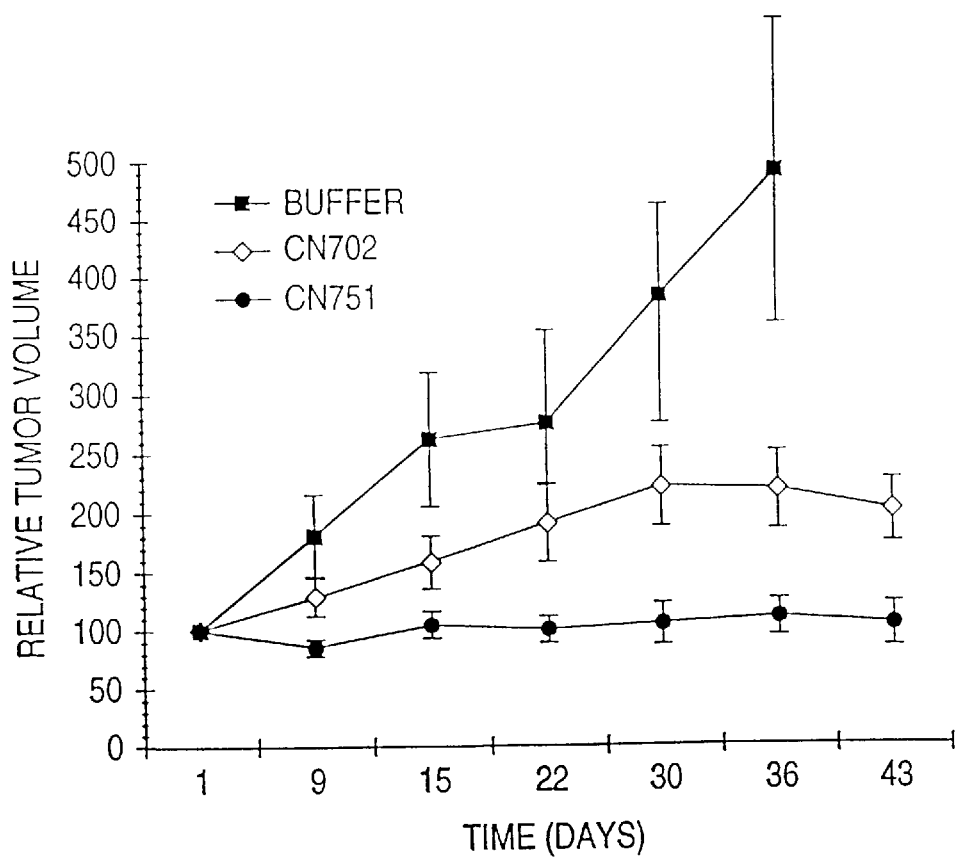
FIG. 14 is a graph comparing tumor volume in mice harboring LNCaP tumor xenografts challenged with CN751 ("H"), CN702 ("J"), or buffer ("B").

LNCaP nude mouse xenografts were challenged with a single intratumoral dose ($1\times10^4$ particles/mm$^3$ tumor) of either CN751, a vector containing the ADP gene, or CN702, a vector lacking the gene. A third group of tumors was treated with buffer alone. The tumors were monitored weekly for six weeks and their relative volume was graphed against time. The results are shown in FIG. 14. Error bars represent the standard error for each sample group. The initial average tumor volume for CN751 treated animals (n=14) was 320 mm$^3$, 322 mm$^3$ for CN702 treated (n=14), and 343 mm$^3$ for buffer treated (n=8). The data suggest that CN751 kills tumor cells more effectively than CN702. On average, tumors challenged with CN751 remained the same size throughout the course of the experiments while nine out of fourteen tumors (64%) regressed. Those treated with CN702 doubled in size. Buffer treated tumors grew to nearly five times their initial volume. The Students T-test indicates that the difference in tumor size between CN751 and CN702 treated tumors was statistically significant from day 9 (p=0.016) through the end of the experiment (p=0.003).

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A replication-competent adenovirus vector comprising two adenoviral genes essential for replication under transcriptional control of the same α-fetoprotein transcriptional regulatory element (AFP-TRE).

2. The adenovirus vector of claim 1, wherein the adenovirus genes essential for replication are selected from the group consisting of E1A, E1B and E4.

3. The adenovirus vector of claim 1, wherein the AFP-TRE comprises an enhancer from an AFP gene.

4. The adenovirus vector of claim 1, wherein the AFP-TRE comprises a promoter from a AFP gene.

5. The adenovirus vector of claim 1, wherein the AFP-TRE comprises an AFP promoter and an AFP enhancer.

6. A method of propagating adenovirus, specific for cells which allow an AFP-TRE to function, said method comprising combining an adenovirus according to claim 1 with cells which allow an AFP-TRE to function, whereby said adenovirus is propagated.

7. The adenovirus vector of claim 1, further comprising a third adenoviral gene under transcriptional control of a cell-specific TRE.

8. A composition comprising an adenovirus of claim 1 and a pharmaceutically acceptable excipient.

9. A host cell comprising the adenoviral vector of claim 1.

10. The adenovirus vector of claim 9, wherein the adenovirus genes are E1A and E1B.

11. The adenovirus vector of claim 3, wherein the enhancer comprises nucleotides from about 1 to about 300 of SEQ ID NO: 1.

12. The adenovirus vector of claim 3, wherein the AFP-TRE comprises nucleotides from about 300 to about 600 of SEQ ID NO: 1.

13. The adenovirus vector of claim 3, wherein the AFP-TRE comprises nucleotides from about 1 to about 600 of SEQ ID NO: 1.

14. The adenovirus vector of claim 4, wherein the AFP-TRE comprises nucleotides from about 600 to about 827 of SEQ ID NO: 1.

15. The adenovirus vector of claim 5, wherein the AFP-TRE comprises SEQ ID NO: 1.

16. The adenovirus vector of claim 5, wherein the AFP-TRE comprises SEQ ID NO: 2.

17. The adenoviral vector of claim 7, wherein the cell-specific TRE is prostate-cell specific.

18. The adenoviral vector of claim 7, wherein the cell-specific TRE is an AFP-TRE.

19. A host cell comprising the adenoviral vector of claim 7.

20. A composition comprising an adenovirus of claim 7 and a pharmaceutically acceptable excipient.

21. A method of propagating adenovirus, specific for cells which allow an AFP-TRE to function, said method comprising combining an adenovirus according to claim 7 with cells which allow an AFP-TRE to function, whereby said adenovirus is propagated.

22. The adenoviral vector of claim 17, wherein the prostate-cell specific TRE is derived from the prostate specific antigen gene, the human kallikrien gene, or the probasin gene.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 822 base pairs
      (B) TYPE: nucleic acid
      (C) STRANDEDNESS: single
      (D) TOPOLOGY: linear (xi) SEQUENCE DESCRIPTION: SEQ ID NO: 1:

```
GCATTGCTGT GAACTCTGTA CTTAGGACTA AACTTTGAGC AATAACACAC ATAGATTGAG      60

GATTGTTTGC TGTTAGCATA CAAACTCTGG TTCAAAGCTC CTCTTTATTG CTTGTCTTGG     120

AAAATTTGCT GTTCTTCATG GTTTCTCTTT TCACTGCTAT CTATTTTTCT CAACCACTCA     180

CATGGCTACA ATAACTGTCT GCAAGCTTAT GATTCCCAAA TATCTATCTC TAGCCTCAAT     240

CTTGTTCCAG AAGATAAAAA GTAGTATTCA AATGCACATC AACGTCTCCA CTTGGAGGGC     300

TTAAAGACGT TTCAACATAC AAACCGGGGA GTTTTGCCTG GAATGTTTCC TAAAATGTGT     360

CCTGTAGCAC ATAGGGTCCT CTTGTTCCTT AAAATCTAAT TACTTTTAGC CCAGTGCTCA     420

TCCCACCTAT GGGGAGATGA GAGTGAAAAG GGAGCCTGAT TAATAATTAC ACTAAGTCAA     480

TAGGCATAGA GCCAGGACTG TTTGGGTAAA CTGGTCACTT TATCTTAAAC TAAATATATC     540

CAAAACTGAA CATGTACTTA GTTACTAAGT CTTTGACTTT ATCTCATTCA TACCACTCAG     600

CTTTATCCAG GCCACTTATG AGCTCTGTGT CCTTGAACAT AAAATACAAA TAACCGCTAT     660

GCTGTTAATT ATTGGCAAAT GTCCCATTTT CAACCTAAGG AAATACCATA AAGTAACAGA     720

TATACCAACA AAAGGTTACT AGTTAACAGG CATTGCCTGA AAAGAGTATA AAAGAATTTC     780

AGCATGATTT TCCATATTGT GCTTCCACCA CTGCCAATAA CA                       822
```

(2) INFORMATION FOR SEQ ID NO: 2:

(i) SEQUENCE CHARACTERISTICS:
      (A) LENGTH: 5224 base pairs
      (B) TYPE: nucleic acid
      (C) STRANDEDNESS: single
      (D) TOPOLOGY: linear (xi) SEQUENCE DESCRIPTION: SEQ ID NO: 2:

```
GAATTCTTAG AAATATGGGG GTAGGGGTGG TGGTGGTAAT TCTGTTTTCA CCCCATAGGT      60

GAGATAAGCA TTGGGTTAAA TGTGCTTTCA CACACACATC ACATTTCATA AGAATTAAGG     120

AACAGACTAT GGGCTGGAGG ACTTTGAGGA TGTCTGTCTC ATAACACTTG GGTTGTATCT     180

GTTCTATGGG GCTTGTTTTA AGCTTGGCAA CTTGCAACAG GGTTCACTGA CTTTCTCCCC     240

AAGCCCAAGG TACTGTCCTC TTTTCATATC TGTTTTGGGG CCTCTGGGGC TTGAATATCT     300

GAGAAAATAT AAACATTTCA ATAATGTTCT GTGGTGAGAT GAGTATGAGA GATGTGTCAT     360
```

```
                                                        -continued
TCATTTGTAT CAATGAATGA ATGAGGACAA TTAGTGTATA AATCCTTAGT ACAACAATCT      420

GAGGGTAGGG GTGGTACTAT TCAATTTCTA TTTATAAAGA TACTTATTTC TATTTATTTA      480

TGCTTGTGAC AAATGTTTTG TTCGGGACCA CAGGAATCAC AAAGATGAGT CTTTGAATTT      540

AAGAAGTTAA TGGTCCAGGA ATAATTACAT AGCTTACAAA TGACTATGAT ATACCATCAA      600

ACAAGAGGTT CCATGAGAAA ATAATCTGAA AGGTTTAATA AGTTGTCAAA GGTGAGAGGG      660

CTCTTCTCTA GCTAGAGACT AATCAGAAAT ACATTCAGGG ATAATTATTT GAATAGACCT      720

TAAGGGTTGG GTACATTTTG TTCAAGCATT GATGGGAAG GAGAGTGAAT ATTTGAAAAC       780

ATTTTCAACT AACCAACCAC CCAATCCAAC AAACAAAAAA TGAAAGAAT CTCAGAAACA       840

GTGAGATAAG AGAAGGAATT TTCTCACAAC CCACACGTAT AGCTCAACTG CTCTGAAGAA      900

GTATATATCT AATATTTAAC ACTAACATCA TGCTAATAAT GATAATAATT ACTGTCATTT      960

TTTAATGTCT ATAAGTACCA GGCATTTAGA AGATATTATT CCATTTATAT ATCAAAATAA     1020

ACTTGAGGGG ATAGATCATT TTCATGATAT ATGAGAAAAA TTAAAAACAG ATTGAATTAT     1080

TTGCCTGTCA TACAGCTAAT AATTGACCAT AAGACAATTA GATTTAAATT AGTTTTGAAT     1140

CTTTCTAATA CCAAAGTTCA GTTACTGTT CCATGTTGCT TCTGAGTGGC TTCACAGACT      1200

TATGAAAAAG TAAACGGAAT CAGAATTACA TCAATGCAAA AGCATTGCTG TGAACTCTGT     1260

ACTTAGGACT AAACTTTGAG CAATAACACA CATAGATTGA GGATTGTTTG CTGTTAGCAT     1320

ACAAACTCTG GTTCAAAGCT CCTCTTTATT GCTTGTCTTG GAAAATTTGC TGTTCTTCAT     1380

GGTTTCTCTT TTCACTGCTA TCTATTTTTC TCAACCACTC ACATGGCTAC AATAACTGTC     1440

TGCAAGCTTA TGATTCCCAA ATATCTATCT CTAGCCTCAA TCTTGTTCCA GAAGATAAAA     1500

AGTAGTATTC AAATGCACAT CAACGTCTCC ACTTGGAGGG CTTAAAGACG TTTCAACATA     1560

CAAACCGGGG AGTTTTGCCT GGAATGTTTC CTAAAATGTG TCCTGTAGCA CATAGGGTCC     1620

TCTTGTTCCT TAAAATCTAA TTACTTTTAG CCCAGTGCTC ATCCCACCTA TGGGGAGATG     1680

AGAGTGAAAA GGGAGCCTGA TTAATAATTA CACTAAGTCA ATAGGCATAG AGCCAGGACT     1740

GTTTGGGTAA ACTGGTCACT TTATCTTAAA CTAAATATAT CCAAAACTGA ACATGTACTT     1800

AGTTACTAAG TCTTTGACTT TATCTCATTC ATACCACTCA GCTTTATCCA GGCCACTTAT     1860

TTGACAGTAT TATTGCGAAA ACTTCCTAAC TGGTCTCCTT ATCATAGTCT TATCCCCTTT     1920

TGAAACAAAA GAGACAGTTT CAAAATACAA ATATGATTTT TATTAGCTCC CTTTTGTTGT     1980

CTATAATAGT CCCAGAAGGA GTTATAAACT CCATTTAAAA AGTCTTTGAG ATGTGGCCCT     2040

TGCCAACTTT GCCAGGAATT CCCAATATCT AGTATTTTCT ACTATTAAAC TTTGTGCCTC     2100

TTCAAAACTG CATTTCTCT CATTCCCTAA GTGTGCATTG TTTTCCCTTA CCGGTTGGTT      2160

TTTCCACCAC CTTTTACATT TTCCTGGAAC ACTATACCCT CCCTCTTCAT TTGGCCCACC     2220

TCTAATTTTC TTTCAGATCT CCATGAAGAT GTTACTTCCT CCAGGAAGCC TTATCTGACC     2280

CCTCCAAAGA TGTCATGAGT TCCTCTTTTC ATTCTACTAA TCACAGCATC CATCACACCA     2340

TGTTGTGATT ACTGATACTA TTGTCTGTTT CTCTGATTAG GCAGTAAGCT CAACAAGAGC     2400

TACATGGTGC CTGTCTCTTG TTGCTGATTA TTCCCATCCA AAAACAGTGC CTGGAATGCA     2460

GACTTAACAT TTTATTGAAT GAATAAATAA ACCCCATCT ATCGAGTGCT ACTTTGTGCA      2520

AGACCCGGTT CTGAGGCATT TATATTTATT GATTATTTA ATTCTCATTT AACCATGAAG      2580

GAGGTACTAT CACTATCCTT ATTTTATAGT TGATAAAGAT AAAGCCCAGA GAAATGAATT     2640

AACTCACCCA AAGTCATGTA GCTAAGTGAC AGGGCAAAAA TTCAAACCAG TTCCCCAACT     2700

TTACGTGATT AATACTGTGC TATACTGCCT CTCTGATCAT ATGGCATGGA ATGCAGACAT     2760
```

```
CTGCTCCGTA AGGCAGAATA TGGAAGGAGA TTGGAGGATG ACACAAAACC AGCATAATAT     2820

CAGAGGAAAA GTCCAAACAG GACCTGAACT GATAGAAAAG TTGTTACTCC TGGTGTAGTC     2880

GCATCGACAT CTTGATGAAC TGGTGGCTGA CACAACATAC ATTGGCTTGA TGTGTACATA     2940

TTATTTGTAG TTGTGTGTGT ATTTTTATAT ATATATTTGT AATATTGAAA TAGTCATAAT     3000

TTACTAAAGG CCTACCATTT GCCAGGCATT TTTACATTTG TCCCCTCTAA TCTTTTGATG     3060

AGATGATCAG ATTGGATTAC TTGGCCTTGA AGATGATATA TCTACATCTA TATCTATATC     3120

TATATCTATA TCTATATCTA TATCTATATC TATATCTATA TATGTATATC AGAAAAGCTG     3180

AAATATGTTT TGTAAAGTTA TAAAGATTTC AGACTTTATA GAATCTGGGA TTTGCCAAAT     3240

GTAACCCCTT TCTCTACATT AAACCCATGT TGGAACAAAT ACATTTATTA TTCATTCATC     3300

AAATGTTGCT GAGTCCTGGC TATGAACCAG ACACTGTGAA AGCCTTTGGG ATATTTTGCC     3360

CATGCTTGGG CAAGCTTATA TAGTTTGCTT CATAAAACTC TATTTCAGTT CTTCATAACT     3420

AATACTTCAT GACTATTGCT TTTCAGGTAT TCCTTCATAA CAAATACTTT GGCTTTCATA     3480

TATTTGAGTA AAGTCCCCCT TGAGGAAGAG TAGAAGAACT GCACTTTGTA AATACTATCC     3540

TGGAATCCAA ACGGATAGAC AAGGATGGTG CTACCTCTTT CTGGAGAGTA CGTGAGCAAG     3600

GCCTGTTTTG TTAACATGTT CCTTAGGAGA CAAAACTTAG GAGAGACACG CATAGCAGAA     3660

AATGGACAAA AACTAACAAA TGAATGGGAA TTGTACTTGA TTAGCATTGA AGACCTTGTT     3720

TATACTATGA TAAATGTTTG TATTTGCTGG AAGTGCTACT GACGGTAAAC CCTTTTTGTT     3780

TAAATGTGTG CCCTAGTAGC TTGCAGTATG ATCTATTTTT TAAGTACTGT ACTTAGCTTA     3840

TTTAAAAATT TTATGTTTAA AATTGCATAG TGCTCTTTCA TTGAAGAAGT TTTGAGAGAG     3900

AGATAGAATT AAATTCACTT ATCTTACCAT CTAGAGAAAC CCAATGTTAA AACTTTGTTG     3960

TCCATTATTT CTGTCTTTTA TTCAACATTT TTTTTAGAGG GTGGGAGGAA TACAGAGGAG     4020

GTACAATGAT ACACAAATGA GAGCACTCTC CATGTATTGT TTTGTCCTGT TTTTCAGTTA     4080

ACAATATATT ATGAGCATAT TTCCATTTCA TTAAATATTC TTCCACAAAG TTATTTTGAT     4140

GGCTGTATAT CACCCTACTT TATGAATGTA CCATATTAAT TTATTTCCTG GTGTGGGTTA     4200

TTTGATTTTA TAATCTTACC TTTAGAATAA TGAAACACCT GTGAAGCTTT AGAAAATACT     4260

GGTGCCTGGG TCTCAACTCC ACAGATTCTG ATTTAACTGG TCTGGGTTAC AGACTAGGCA     4320

TTGGGAATTC AAAAAGTTCC CCCAGTGATT CTAATGTGTA GCCAAGATCG GGAACCCTTG     4380

TAGACAGGGA TGATAGGAGG TGAGCCACTC TTAGCATCCA TCATTTAGTA TTAACATCAT     4440

CATCTTGAGT TGCTAAGTGA ATGATGCACC TGACCCACTT TATAAAGACA CATGTGCAAA     4500

TAAAATTATT ATAGGACTTG GTTTATTAGG GCTTGTGCTC TAAGTTTTCT ATGTTAAGCC     4560

ATACATCGCA TACTAAATAC TTTAAAATGT ACCTTATTGA CATACATATT AAGTGAAAAG     4620

TGTTTCTGAG CTAAACAATG ACAGCATAAT TATCAAGCAA TGATAATTTG AAATGAATTT     4680

ATTATTCTGC AACTTAGGGA CAAGTCATCT CTCTGAATTT TTTGTACTTT GAGAGTATTT     4740

GTTATATTTG CAAGATGAAG AGTCTGAATT GGTCAGACAA TGTCTTGTGT GCCTGGCATA     4800

TGATAGGCAT TTAATAGTTT TAAAGAATTA ATGTATTTAG ATGAATTGCA TACCAAATCT     4860

GCTGTCTTTT CTTTATGGCT TCATTAACTT AATTTGAGAG AAATTAATTA TTCTGCAACT     4920

TAGGGACAAG TCATGTCTTT GAATATTCTG TAGTTTGAGG AGAATATTTG TTATATTTGC     4980

AAAATAAAAT AAGTTTGCAA GTTTTTTTTT TCTGCCCCAA AGAGCTCTGT GTCCTTGAAC     5040

ATAAAATACA AATAACCGCT ATGCTGTTAA TTATTGGCAA ATGTCCCATT TTCAACCTAA     5100
```

```
GGAAATACCA TAAAGTAACA GATATACCAA CAAAAGGTTA CTAGTTAACA GGCATTGCCT    5160

GAAAAGAGTA TAAAAGAATT TCAGCATGAT TTTCCATATT GTGCTTCCAC CACTGCCAAT    5220

AACA                                                                 5224

(2) INFORMATION FOR SEQ ID NO: 3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 3:

TCGTCTTCAA GAATTCTCA                                                    19

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 4:

TTTCAGTCAC CGGTGTCGGA                                                   20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 5:

GCATTCTCTA GACACAGGTG                                                   20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 6:

TCCGACACCG GTGACTGAAA                                                   20

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

GCCCACGGCC GCATTATATA C                                                 21

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

(xi) SEQUENCE DESCRIPTION: SEQ ID NO: 8:

GTATATAATG CGGCCGTGGG C                                              21

(2) INFORMATION FOR SEQ ID NO: 9:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO: 9:

CCAGAAAATC CAGCAGGTAC C                                              21

(2) INFORMATION FOR SEQ ID NO: 10:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO: 10:

GTGACCGGTG CATTGCTGTG AACTCTGTA                                      29

(2) INFORMATION FOR SEQ ID NO: 11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 11:

ATAAGTGGCC TGGATAAAGC TGAGTGG                                        27

(2) INFORMATION FOR SEQ ID NO: 12:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO: 12:

GTCACCGGTC TTTGTTATTG GCAGTGGT                                       28

(2) INFORMATION FOR SEQ ID NO: 13:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO: 13:

ATCCAGGCCA CTTATGAGCT CTGTGTCCTT                                     30

(2) INFORMATION FOR SEQ ID NO: 14:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 14:

TATCGGCCGG CATTGCTGTG AACTCT                                              26

(2) INFORMATION FOR SEQ ID NO: 15:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (xi) SEQUENCE DESCRIPTION: SEQ ID NO: 15:

TTACGGCCGC TTTGTTATTG GCAGTG                                              26

(2) INFORMATION FOR SEQ ID NO: 16:

(i) SEQUENCE CHARACTERISTICS:
              (A) LENGTH: 29 base pairs
              (B) TYPE: nucleic acid
              (C) STRANDEDNESS: single
              (D) TOPOLOGY: linear (xi) SEQUENCE DESCRIPTION: SEQ ID NO: 16:

GCCTTAATTA AAAGCAAACC TCACCTCCG                                           29

(2) INFORMATION FOR SEQ ID NO: 17:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (xi) SEQUENCE DESCRIPTION: SEQ ID NO: 17:

GTGGAACAAA AGGTGATTAA AAAATCCCAG                                          30

(2) INFORMATION FOR SEQ ID NO: 18:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (xi) SEQUENCE DESCRIPTION: SEQ ID NO: 18:

CACCTTTTGT TCCACCGCTC TGCTTATTAC                                          30

(2) INFORMATION FOR SEQ ID NO: 19:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (xi) SEQUENCE DESCRIPTION: SEQ ID NO: 19:

GGCTTAATTA ACTGTGAAAG GTGGGAGC                                            28

(2) INFORMATION FOR SEQ ID NO: 20:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (xi) SEQUENCE DESCRIPTION: SEQ ID NO: 20:

```
GCAGCTCACT TAAGTTCATG TCG                                          23
```

(2) INFORMATION FOR SEQ ID NO: 21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 21:

```
TCAGCCTAGG AAATATGACT ACGTCCG                                      27
```

(2) INFORMATION FOR SEQ ID NO: 22:

(i) SEQUENCE CHARACTERISTICS:
        (A) LENGTH: 307 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 2..304

(xi) SEQUENCE DESCRIPTION: SEQ ID NO: 22:

```
G ATG ACC GGC TCA ACC ATC GCG CCC ACA ACG GAC TAT CGC AAC ACC        46
  Met Thr Gly Ser Thr Ile Ala Pro Thr Thr Asp Tyr Arg Asn Thr
  1               5                   10                  15

ACT GCT ACC GGA CTA ACA TCT GCC CTA AAT TTA CCC CAA GTT CAT GCC      94
Thr Ala Thr Gly Leu Thr Ser Ala Leu Asn Leu Pro Gln Val His Ala
                20                  25                  30

TTT GTC AAT GAC TGG GCG AGC TTG GAC ATG TGG TGG TTT TCC ATA GCG     142
Phe Val Asn Asp Trp Ala Ser Leu Asp Met Trp Trp Phe Ser Ile Ala
            35                  40                  45

CTT ATG TTT GTT TGC CTT ATT ATT ATG TGG CTT ATT TGT TGC CTA AAG     190
Leu Met Phe Val Cys Leu Ile Ile Met Trp Leu Ile Cys Cys Leu Lys
        50                  55                  60

CGC AGA CGC GCC AGA CCC CCC ATC TAT AGG CCT ATC ATT GTG CTC AAC     238
Arg Arg Arg Ala Arg Pro Pro Ile Tyr Arg Pro Ile Ile Val Leu Asn
    65                  70                  75

CCA CAC AAT GAA AAA ATT CAT AGA TTG GAC GGT CTG AAA CCA TGT TCT     286
Pro His Asn Glu Lys Ile His Arg Leu Asp Gly Leu Lys Pro Cys Ser
80                  85                  90                  95

CTT CTT TTA CAG TAT GAT TAA                                         307
Leu Leu Leu Gln Tyr Asp
                100
```

(2) INFORMATION FOR SEQ ID NO: 23:

(i) SEQUENCE CHARACTERISTICS:
        (A) LENGTH: 101 amino acids
        (B) TYPE: amino acid
        (D) TOPOLOGY: linear (ii) MOLECULE TYPE: protein (xi) SEQUENCE DESCRIPTION: SEQ ID NO: 23:

```
Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Val His Ala Phe
                20                  25                  30

Val Asn Asp Trp Ala Ser Leu Asp Met Trp Trp Phe Ser Ile Ala Leu
            35                  40                  45
```

```
Met Phe Val Cys Leu Ile Ile Met Trp Leu Ile Cys Cys Leu Lys Arg
         50                  55                 60

Arg Arg Ala Arg Pro Pro Ile Tyr Arg Pro Ile Ile Val Leu Asn Pro
 65             70                  75                      80

His Asn Glu Lys Ile His Arg Leu Asp Gly Leu Lys Pro Cys Ser Leu
             85                  90                 95

Leu Leu Gln Tyr Asp
            100
```